United States Patent
Hee-Hanson et al.

(10) Patent No.: US 12,343,511 B1
(45) Date of Patent: Jul. 1, 2025

(54) MEDICAMENT DELIVERY DEVICE

(71) Applicant: Genzyme Corporation, Cambridge, MA (US)

(72) Inventors: Alexander Hee-Hanson, Melbourn (GB); Michael Parrott, Melbourn (GB); Nicholas Harding, Melbourn (GB); Robert Wilson, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/640,427

(22) Filed: Apr. 19, 2024

(51) Int. Cl.
*A61M 5/315* (2006.01)
*A61M 5/32* (2006.01)
*A61M 5/20* (2006.01)

(52) U.S. Cl.
CPC ...... *A61M 5/31566* (2013.01); *A61M 5/3243* (2013.01); *A61M 2005/2073* (2013.01); *A61M 2005/208* (2013.01)

(58) Field of Classification Search
CPC ........ A61M 2005/208; A61M 2205/75; A61M 39/105; A61M 2039/0027; A61M 2039/1016; A61M 2039/1033; A61M 2039/1077; A61M 2039/242; A61M 2005/2073
See application file for complete search history.

(56) References Cited

U.S. PATENT DOCUMENTS

| | | |
|---|---|---|
| 2,522,961 A | 9/1950 | William |
| 2,633,267 A | 3/1953 | Lebus |
| 3,886,513 A * | 5/1975 | Smith ............ F03G 7/06 60/516 |
| 4,801,295 A | 1/1989 | Spencer |
| 5,045,062 A | 9/1991 | Henson |

(Continued)

FOREIGN PATENT DOCUMENTS

| | | |
|---|---|---|
| DE | 3921747 A1 | 1/1991 |
| EP | 3501577 A1 | 6/2019 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Michael J Tsai
*Assistant Examiner* — Justin L Zamory
(74) *Attorney, Agent, or Firm* — Fish & Richardson P.C.

(57) ABSTRACT

A medicament delivery device includes an actuator including an actuation member configured to be movable by a user to an actuation position to cause a dose of medicament to be dispensed from the medicament delivery device. The actuator is configured to be movable from a deactivated position in which a user is prevented from moving the actuation member to the actuation position to an activated position in which the actuation member is released for movement by a user to the actuation position. The device includes a temperature-dependent actuator configured to move the actuator from the deactivated position to the activated position in response to a change in temperature of the temperature-dependent actuator.

30 Claims, 10 Drawing Sheets

(56) References Cited

U.S. PATENT DOCUMENTS

| | | |
|---|---|---|
| 5,176,275 A | 1/1993 | Bowie |
| 5,328,484 A | 7/1994 | Somers et al. |
| 5,396,051 A | 3/1995 | Kuhn et al. |
| 5,478,316 A | 12/1995 | Bitdinger et al. |
| 5,505,324 A | 4/1996 | Danico |
| 5,505,706 A | 4/1996 | Maus et al. |
| 5,536,917 A | 7/1996 | Suppelsa et al. |
| 5,622,274 A | 4/1997 | Bright |
| 5,738,658 A | 4/1998 | Maus et al. |
| 5,984,899 A | 11/1999 | D'Alessio et al. |
| 6,080,461 A | 6/2000 | Wozniak et al. |
| 6,394,985 B1 | 5/2002 | Lin |
| 7,762,981 B2 | 7/2010 | Dacquay et al. |
| 7,887,506 B1 | 2/2011 | Smolyarov et al. |
| 7,918,824 B2 | 4/2011 | Bishop et al. |
| 8,133,198 B2 | 3/2012 | Neer |
| 8,409,138 B2 | 4/2013 | James et al. |
| 8,734,394 B2 | 5/2014 | Adams et al. |
| 9,044,553 B2 | 6/2015 | James et al. |
| 9,402,957 B2 | 8/2016 | Adams et al. |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 11,298,462 B2 | 4/2022 | Atterbury et al. |
| 11,331,432 B2 | 5/2022 | Holmqvist et al. |
| 11,369,751 B2 | 6/2022 | Ruan et al. |
| 11,452,821 B2 | 9/2022 | LaFever et al. |
| 2002/0055712 A1 | 5/2002 | Neracher |
| 2004/0039336 A1 | 2/2004 | Amark et al. |
| 2005/0101919 A1 | 5/2005 | Brunnberg |
| 2005/0273061 A1 | 12/2005 | Hommann et al. |
| 2006/0224124 A1 | 10/2006 | Scherer |
| 2007/0270777 A1 | 11/2007 | Dacquay et al. |
| 2008/0097311 A1 | 4/2008 | Dacquay et al. |
| 2008/0097390 A1 | 4/2008 | Dacquay et al. |
| 2008/0269692 A1 | 10/2008 | James et al. |
| 2009/0036868 A1 | 2/2009 | Pinedjian et al. |
| 2009/0281496 A1 | 11/2009 | Matusch |
| 2010/0211005 A1 | 8/2010 | Edwards et al. |
| 2011/0054414 A1 | 3/2011 | Shang et al. |
| 2011/0144594 A1 | 6/2011 | Sund et al. |
| 2011/0202011 A1 | 8/2011 | Wozencroft |
| 2011/0319813 A1 | 12/2011 | Kamen et al. |
| 2013/0237921 A1 | 9/2013 | Lannan et al. |
| 2013/0267897 A1 | 10/2013 | Kemp et al. |
| 2014/0236076 A1 | 8/2014 | Marshall et al. |
| 2014/0249483 A1 | 9/2014 | Kiilerich et al. |
| 2014/0263156 A1 | 9/2014 | Newsom et al. |
| 2014/0276637 A1 | 9/2014 | Massey, Jr. |
| 2015/0246180 A1* | 9/2015 | Fenlon ............... A61M 5/3135 604/228 |
| 2015/0273162 A1 | 10/2015 | Holmqvist |
| 2016/0001015 A1 | 1/2016 | Kucuk et al. |
| 2016/0354555 A1* | 12/2016 | Gibson ............... A61M 5/2033 |
| 2016/0367763 A1 | 12/2016 | Tschirren et al. |
| 2017/0215699 A1 | 8/2017 | Ouyang et al. |
| 2017/0216526 A1 | 8/2017 | Brereton et al. |
| 2017/0224929 A1 | 8/2017 | Sampson et al. |
| 2017/0246403 A1 | 8/2017 | Cowe et al. |
| 2017/0361034 A1 | 12/2017 | Scheller et al. |
| 2018/0250471 A1 | 9/2018 | Grimoldby et al. |
| 2018/0339114 A1 | 11/2018 | Wendland et al. |
| 2019/0030249 A1 | 1/2019 | Gonzalez et al. |
| 2019/0192785 A1 | 6/2019 | Wendland et al. |
| 2019/0366000 A1 | 12/2019 | Cowe et al. |
| 2020/0114041 A1 | 4/2020 | Alas et al. |
| 2020/0316314 A1 | 10/2020 | Buri et al. |
| 2021/0077732 A1 | 3/2021 | Egelhofer |
| 2021/0196900 A1 | 7/2021 | Apply et al. |
| 2022/0015429 A1* | 1/2022 | Brown ............... A24F 40/57 |
| 2022/0176042 A1 | 6/2022 | Belisle |
| 2022/0395640 A1 | 12/2022 | Schwartzentruber |
| 2023/0001099 A1 | 1/2023 | Dunn |
| 2023/0238105 A1 | 7/2023 | Schneider et al. |
| 2023/0347074 A1 | 11/2023 | Gavin |
| 2024/0009397 A1 | 1/2024 | In et al. |

FOREIGN PATENT DOCUMENTS

| | | |
|---|---|---|
| WO | WO 2002/047746 A1 | 6/2002 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

U.S. Appl. No. 18/640,163, filed Apr. 19, 2024, Alexander Hee-Hanson.

U.S. Appl. No. 18/640,292, filed Apr. 19, 2024, Alexander Hee-Hanson.

U.S. Appl. No. 18/640,600, filed Apr. 19, 2024, Alexander Hee-Hanson.

U.S. Appl. No. 18/640,710, filed Apr. 19, 2024, Alexander Hee-Hanson.

* cited by examiner

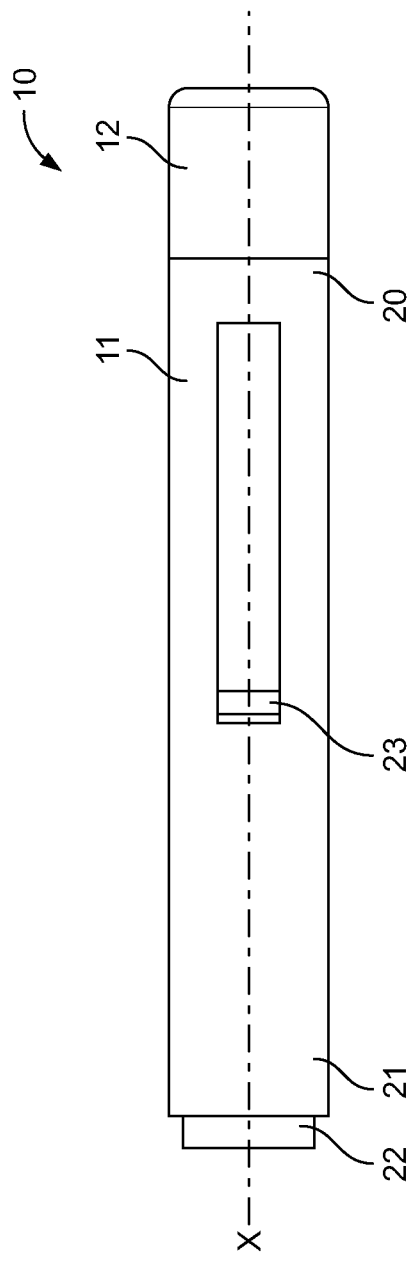
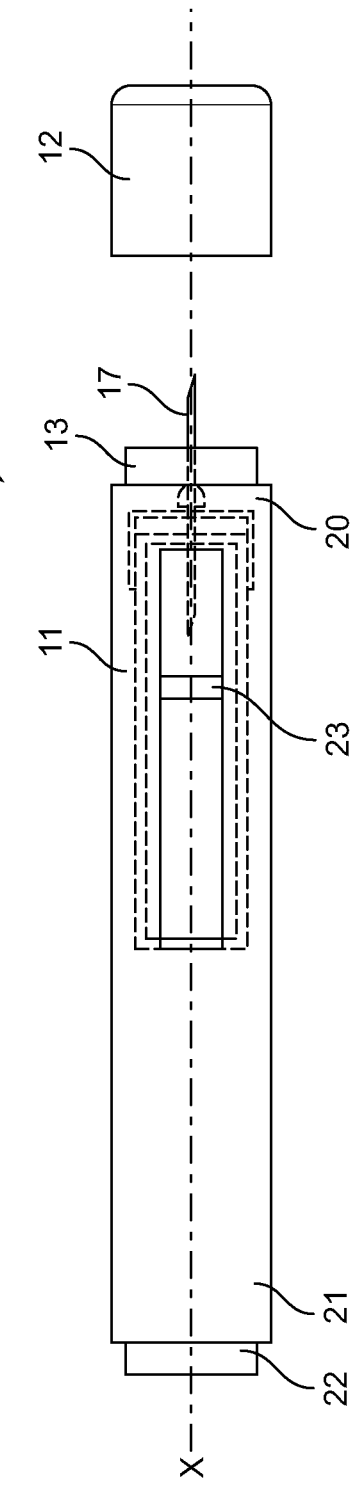
FIG. 1A
FIG. 1B

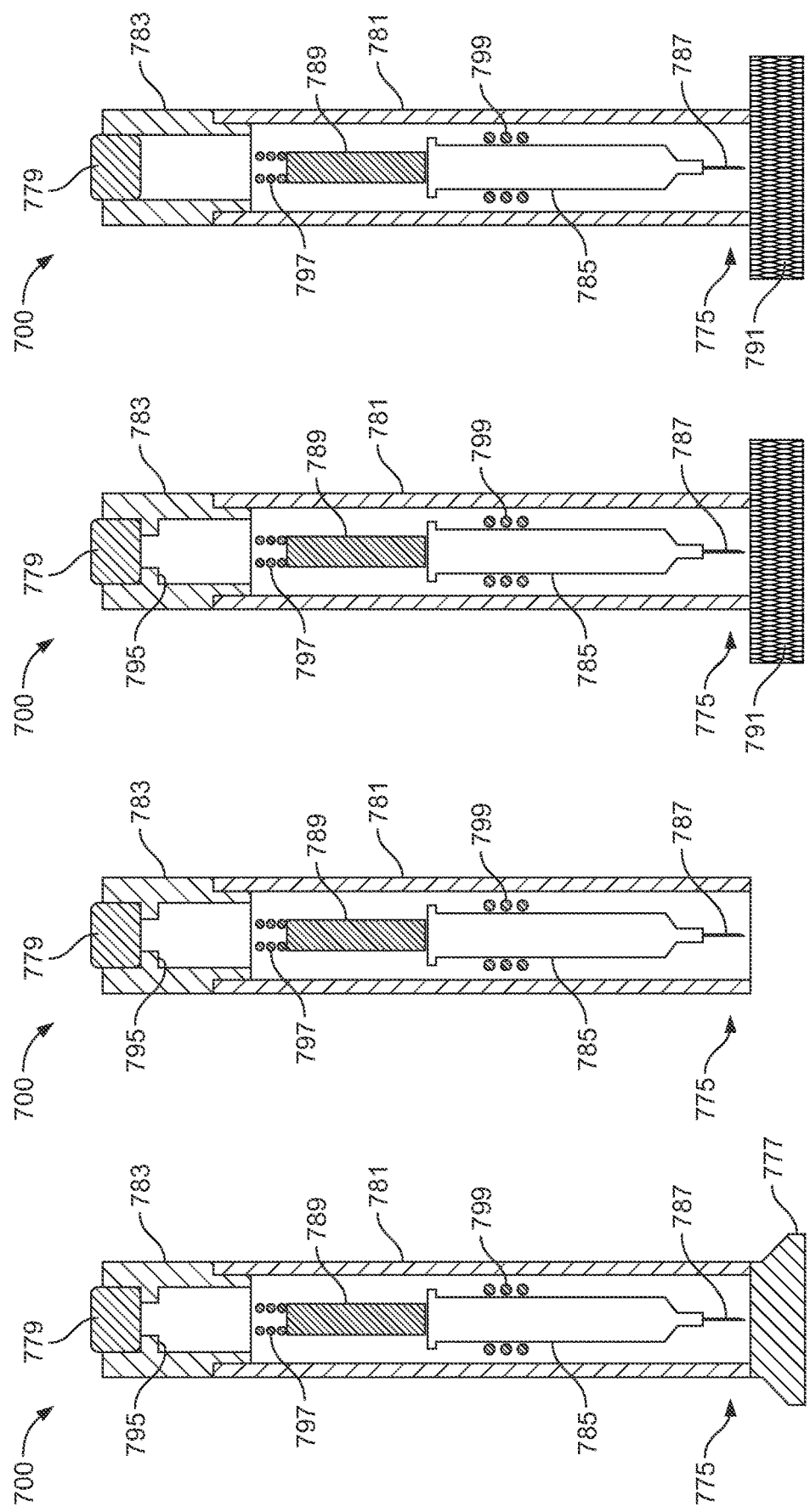

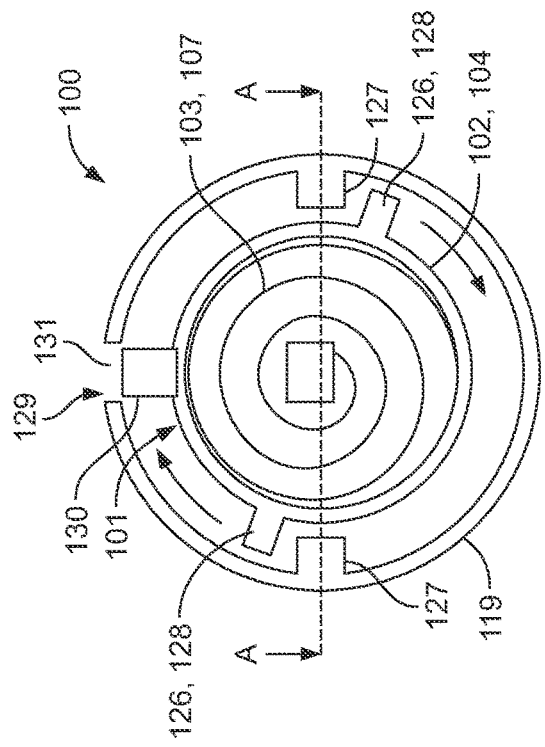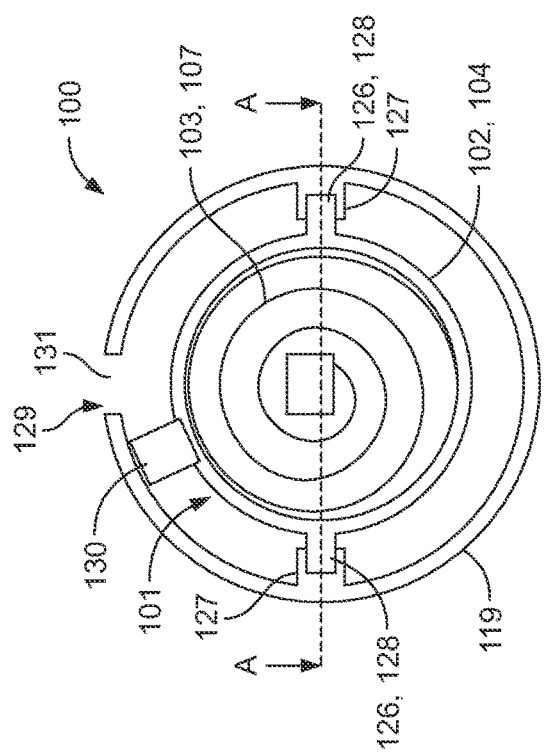
FIG. 3C
FIG. 3A
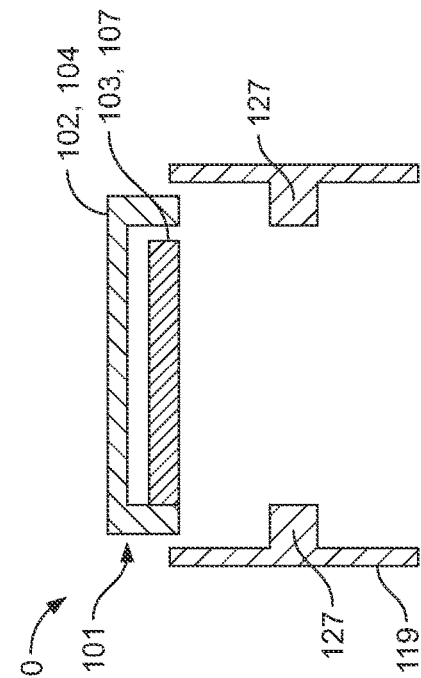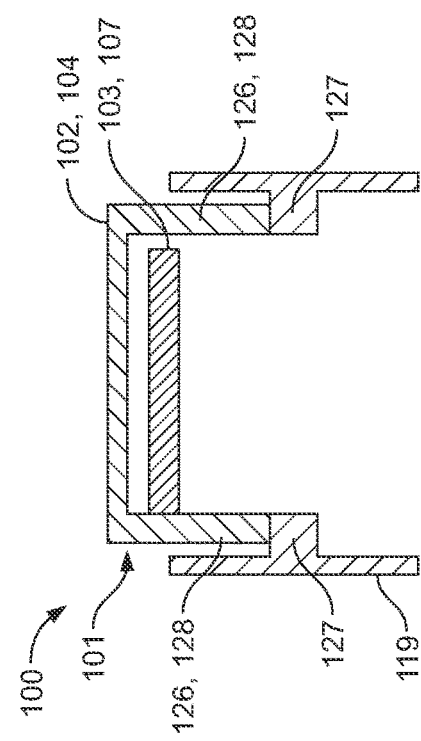
FIG. 3D
FIG. 3B

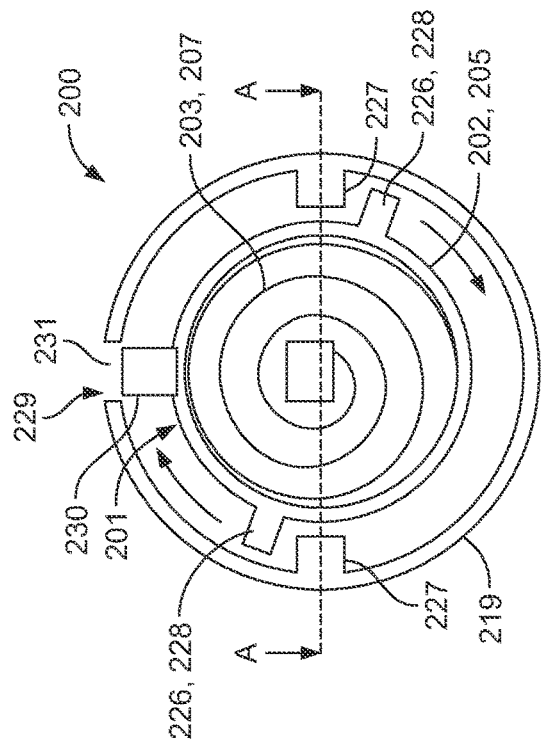
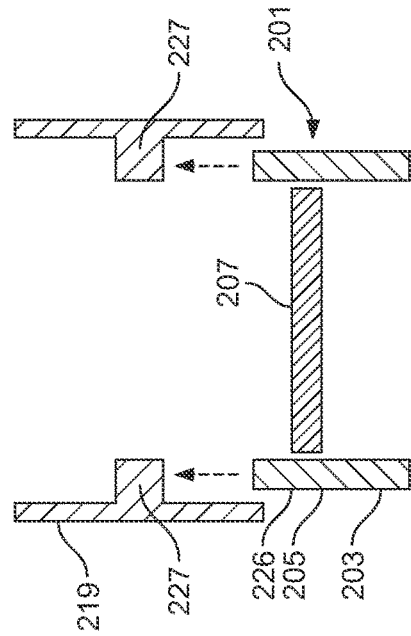
FIG. 4C
FIG. 4D
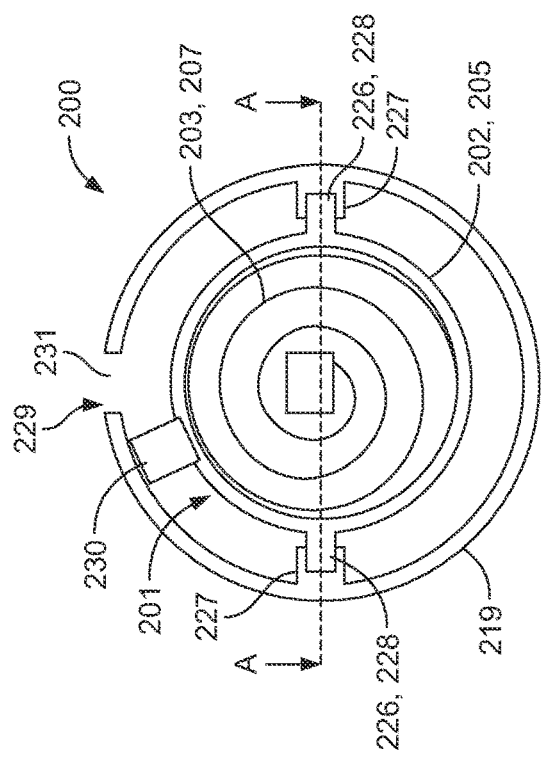
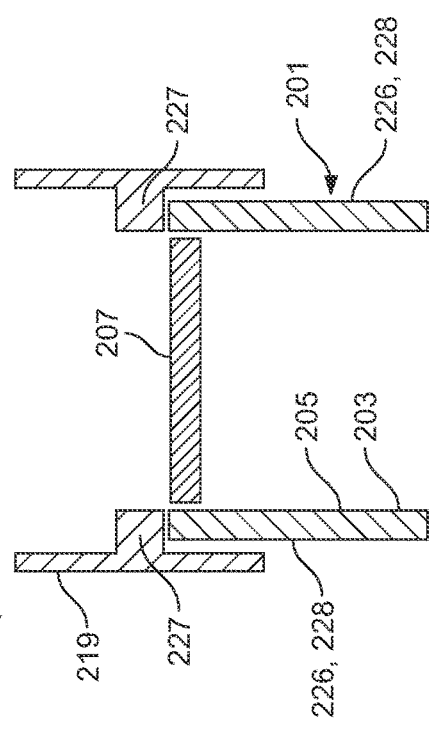
FIG. 4A
FIG. 4B

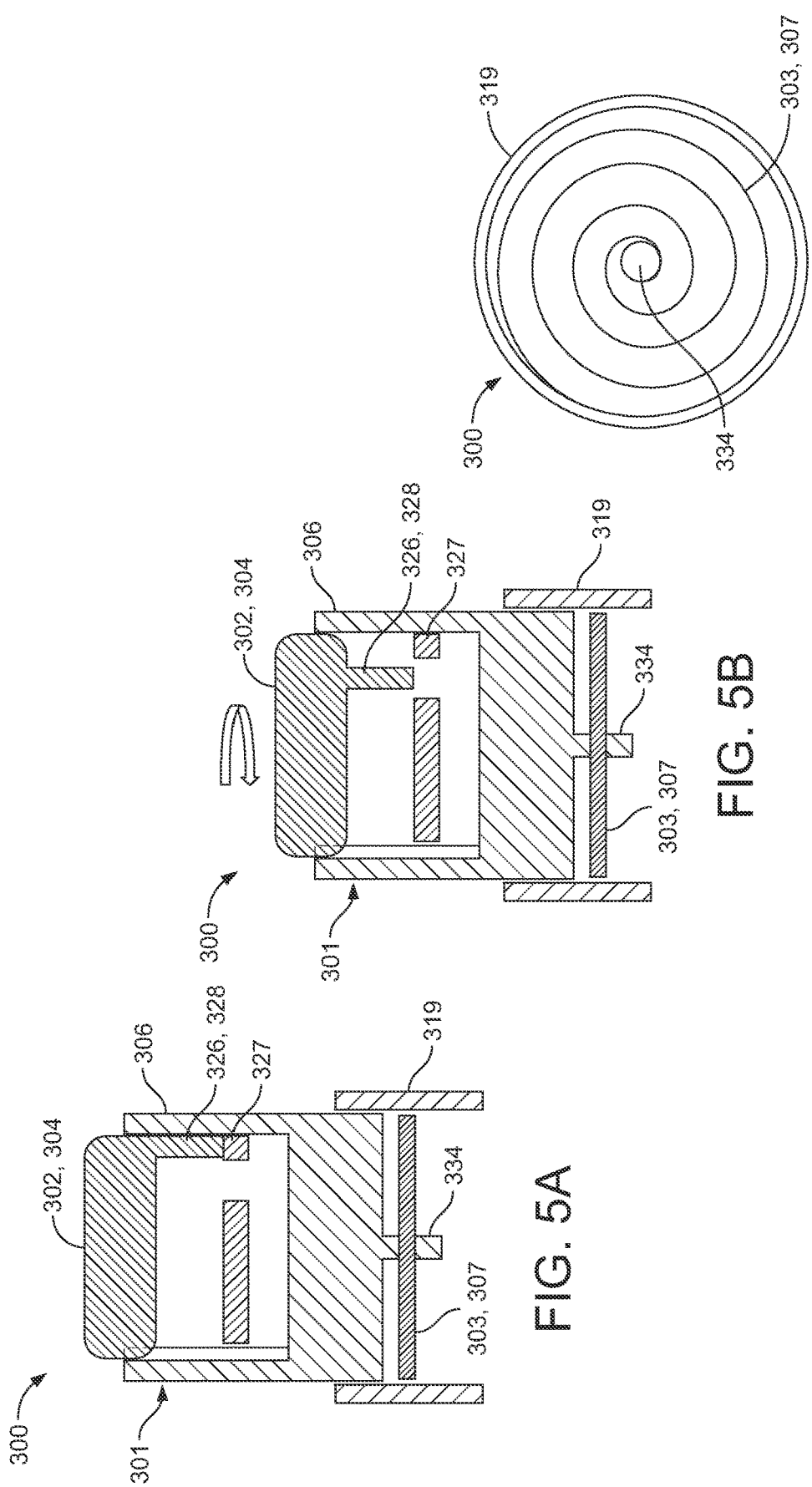

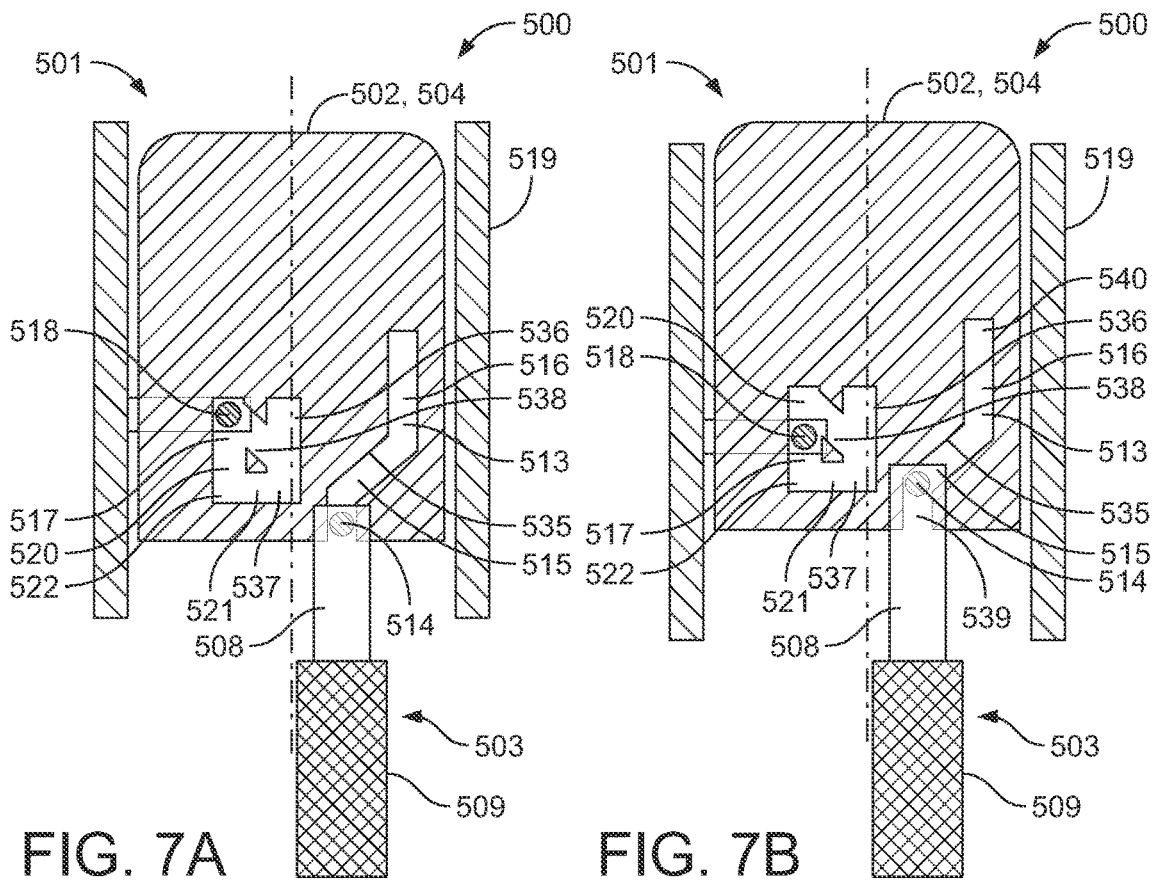
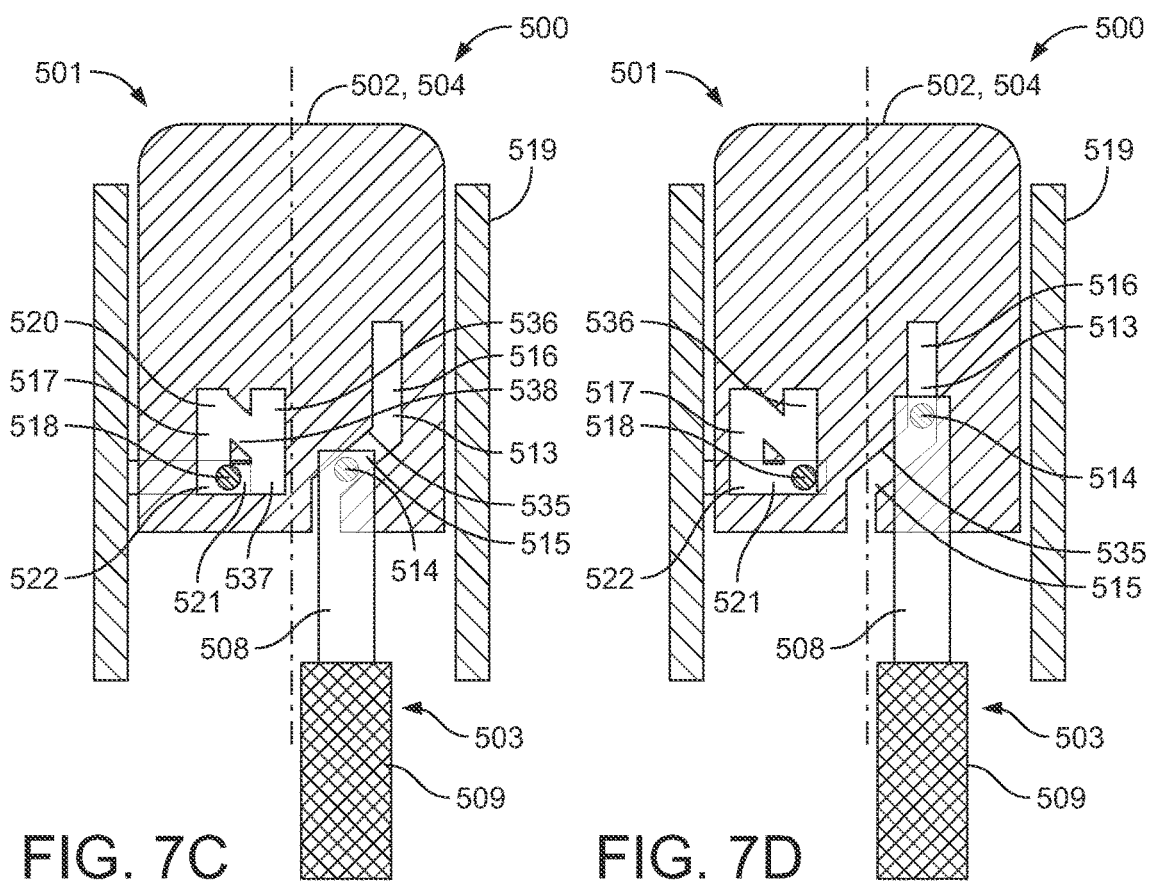

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, dispense medicament to an injection site of a patient.

Some devices may be triggered, and thereby deliver a dose of medicament, when the device is at a sub-optimal temperature. Depending on the particular medicament within the device, some medicament delivery devices are required to be stored at sub-ambient temperatures, for example in a fridge or in a freezer, in order to allow the medicament to be stored for an extended period of time without the medicament losing efficacity. When the medicament is too cold, for example if the device has not been allowed to warm to ambient temperature, the viscosity of the medicament may be increased such that a dose may be dispensed incorrectly or not at all, for example the viscosity of the medicament may be such that the medicament is unable to pass through a needle of the device. Thus, when a user places the device at an injection site and triggers the device, expecting a dose of medicament to be delivered, a dose may not be dispensed or may not be fully dispensed. In some instances, the user may not be aware that a dose was not dispensed at all or that a dose was not fully dispensed. The user may then remove the device from the injection site and the device may then increase in temperature through being passively heated by the external environment, causing the viscosity of the medicament to decrease and causing the already-triggered device to unexpectedly dispense a dose of medicament. Furthermore, the dispensing of medicament when the medicament is too cold can be painful to a recipient or subject of the injection.

SUMMARY

According to a first aspect, a medicament delivery device includes:
an actuator comprising an actuation member configured to be movable by a user to an actuation position to cause a dose of medicament to be dispensed from the medicament delivery device;
the actuator being configured to be movable from a deactivated position (or configuration) in which a user is prevented from moving the actuation member to the actuation position to an activated position (or configuration) in which the actuation member is released for movement by a user to the actuation position; and
a temperature-dependent actuator configured to move the actuator from the deactivated position (or configuration) to the activated position (or configuration) in response to a change in temperature of the temperature-dependent actuator.

In some embodiments, the deactivated position and the activated position of the actuator may instead be a deactivated configuration or an activated configuration of the actuator respectively.

In some embodiments, the actuation member is configured to be depressible by a user to the actuation position to cause a dose of medicament to be dispensed from the medicament delivery device.

In some embodiments, the actuation member comprises or is (e.g. is integrally formed with) the actuator.

In some embodiments, the change in temperature of the temperature-dependent actuator is an increase in the temperature of the temperature-dependent actuator. In some embodiments, the change in temperature of the temperature-dependent actuator is a decrease in the temperature of the temperature-dependent actuator. In some embodiments, the increase or decrease in temperature is 1, 2, 3, 4, 5, 6, 7, 8, 9, 10, 11, 12, 13, 14, 15, 16, 17, 18, 19 or 20 degrees Celsius, or between a range defined by any two of these values.

In some embodiments, the temperature-dependent actuator is configured to move the actuator from the deactivated position to the activated position at or above a predetermined temperature of the temperature-dependent actuator. In some embodiments, the predetermined temperature is 1, 2, 3, 4, 5, 6, 7, 8, 9, 10, 11, 12, 13, 14, 15, 16, 17, 18, 19, 20, 21, 22, 23, 24 or 25 degrees Celsius or is between a range defined by any two of these values.

In some embodiments, the device further comprises a needle for injecting a dose of medicament into a user, the needle being arranged at a distal end of the medicament delivery device and the needle is configured to be axially movable from a retracted position in which the needle is retracted within the medicament delivery device to an exposed position in which the needle is exposed from a distal end of the medicament delivery device for injecting medicament into a user; and, in the actuation position, the actuation member is configured to cause the needle to move from the retracted position to the exposed position.

In some embodiments, the actuation member comprises a button configured to be depressible by a user to the actuation position. In some embodiments, the button is arranged at a proximal end of the device and the button is configured to be depressible by a user in a distal direction of the device to the actuation position. In some embodiments, the actuator comprises or is the button.

In some embodiments, the actuation member comprises a needle sleeve. In some embodiments, the needle sleeve is arranged at a distal end of the device and the needle sleeve is depressible by a user in a proximal direction of the device to the actuation position. In some embodiments, the needle sleeve is configured to cover a needle of the device in an extended position of the needle sleeve and the needle sleeve is configured to be axially movable in a proximal direction of the device for exposing the needle for delivering a dose of medicament. In some embodiments, the actuator is the needle sleeve.

In some embodiments, in the deactivated position, the actuation member is configured to abuttingly engage with a stop fixed relative to a body of the device so as to prevent the actuation member from being moved by a user to the actuation position. In some embodiments, in the activated position, the actuation member is removed from engagement with the stop such that the actuation member is depressible by a user to the actuation position.

In some embodiments, the actuator comprises a locking member configured to be movable from a locking position, in which the locking member is configured to prevent the actuation member from being moved by a user to the actuation position, to a release position in which the locking member is configured to release the actuation member for movement by a user to the actuation position, and the temperature-dependent actuator is configured to move the locking member from the locking position to the release position in response to the change of temperature of the temperature-dependent actuator. In some embodiments, the locking member comprises a lock ring configured to extend circumferentially partially or entirely around a body of the device. In some embodiments, the locking member is substantially annular thereby defining an annulus of the locking member, a longitudinal axis of the annulus is substantially parallel with a longitudinal axis of the device.

In some embodiments, the temperature-dependent actuator is a rotary actuator.

In some embodiments, the temperature-dependent actuator comprises a bimetallic strip (e.g. arranged in a spiral) so as to cause the actuator to rotate (e.g. relative to a body of the device) from the deactivated position to the activated position in response to a change in temperature of the temperature-dependent actuator. In some embodiments, the bimetallic strip comprises a first end operatively connected to the actuation member and a second, opposed end fixed relative to (e.g. operatively connected to) a body of the device.

In some embodiments, the temperature-dependent actuator comprises a piston slidably received within a cylinder. In some embodiments, the cylinder comprises a contained mass of material having a temperature-variable volume such that a change in temperature of the mass of material causes the piston to move relative to the cylinder. In some embodiments, the temperature-dependent actuator is a linear actuator. In some embodiments, the contained mass of material may either increase or decrease with increasing temperature.

In some embodiments, the temperature-dependent actuator comprises a phase change actuator, the phase change actuator comprising a phase change material configured to change phase in response to the change in temperature of the temperature-dependent actuator. In some embodiments, the phase change material is provided in the cylinder. In some embodiments, the phase change material is configured to change from solid to liquid in response to the change in temperature of the temperature-dependent actuator. In some embodiments, the phase change material is configured to change from liquid to gas in response to the change in temperature of the temperature-dependent actuator. In some embodiments, the phase change material is a wax. In some embodiments, the temperature-dependent actuator comprises a wax motor.

In some embodiments, the temperature-dependent actuator is configured to move the actuation member from an initial position (e.g. in which the actuation member is recessed with a body of the device) to a raised position (or protruded position) in response to the change in temperature of the temperature-dependent actuator. In some embodiments, in the raised position, a proximal end of the actuation member protrudes from the proximal end of a body (e.g. a housing) of the device so as to be depressible by a user to the actuation position. In some embodiments, in the initial position, a proximal end of the actuation member is recessed so as to not be depressible by a user to the actuation position. In some embodiments, in the raised position, the actuation member is in the activated position.

In some embodiments, in the raised position, the actuation member is configured to be rotatable to a depressible position in which the actuation member is depressible to the actuation position. In some embodiments, in the raised position, the actuation member is configured to be rotatable by a user to the depressible position.

In some embodiments, the actuation member comprises a drive slot and the temperature-dependent actuator comprises a protrusion (e.g coupled to the piston of the temperature-dependent actuator) slidably received within the drive slot for constraining movement of the protrusion with respect to the drive slot, the drive slot comprises a circumferentially-extending portion and an axially-extending portion such that, when the actuator is in the deactivated position, the protrusion is received within the circumferentially-extending portion of the drive slot such that the temperature-dependent actuator causes the actuation member to move to the raised position in response to the temperature change of the temperature-dependent actuator so as to allow the actuation member to rotate (or to be rotated) to the depressible position to thereby cause the protrusion to enter the axially-extending portion of the drive slot, thereby allowing the actuation member to be depressed by a user from the depressible position to the actuation position. The circumferentially-extending portion may be orthogonal or substantially orthogonal to a longitudinal axis of the device. In some embodiments, the circumferentially-extending portion of the slot comprises an abutment surface and the protrusion is configured to engage the abutment surface when the temperature-dependent actuator moves the actuator from the deactivated position to the activated position to move the actuation member from the initial position to the raised position.

In some embodiments, the circumferentially-extending portion of the drive slot has an axially-extending component of direction for translating axial movement of the protrusion into rotation of the actuation member, e.g. relative to a body of the device, so as to cause the actuation member to rotate to the depressible position.

In some embodiments, the actuation member comprises a guide slot, and the medicament delivery device comprises a guide protrusion which is fixed relative to a body of the device, the guide protrusion is located in the guide slot for constraining movement of the actuation member relative to the body, the guide slot comprising an axially-extending portion, and, when the protrusion is received within the circumferentially-extending portion of the drive slot, the guide protrusion is located in the axially-extending portion of the guide slot for allowing the actuation member to move axially relative to the body as the temperature-dependent actuator moves the actuator from the deactivated position to the activated position.

In some embodiments, the guide slot comprises a circumferentially-extending portion for permitting rotation of the actuation member (e.g. relative to a body of the device), the circumferentially-extending portion of the guide slot has a first end connected to the axially-extending portion of the guide slot, and when the temperature-dependent actuator moves the actuator from the deactivated position to the activated position, the guide protrusion is caused to travel from the axially-extending portion of the guide slot along the circumferentially-extending portion of the guide slot so as to cause the actuation member to rotate as the actuation member moves to the raised position.

In some embodiments, the axially-extending portion of the guide slot is a first axially-extending portion, and the guide slot further comprises a second axially-extending portion connected to a second end of the circumferentially-extending portion of the guide slot for allowing the actuation member to move to the actuation position. In some embodiments, the guide slot comprises a diagonally-extending portion connecting the second axially-extending portion to the first axially-extending portion for allowing the guide protrusion to return to the first axially-extending portion of the guide slot.

In some embodiments, the medicament delivery device further comprises a visual indicator configured to visually indicate to a user when the actuator is in the activated position. In some embodiments, the visual indicator comprises an indication member and a window, and the indication member is movable with respect to the window such that, in the deactivated position, the indication member is not viewable by a user through the window (for example, the indication member is misaligned with the window) and, in the activated position, the indication member is viewable by a user through the window (for example, the indication member is aligned with the window). In some embodiments, the visual indicator is obscured so as not to be viewable by a user in the deactivated position.

In some embodiments, the indication member is operatively coupled to the actuator so as to move therewith from the deactivated position to the activated position.

In some embodiments, the device further comprises a needle for injecting medicament into a user, the needle is movable relative to a body of the device from a pre-use position to an injecting position, and in the pre-use position the distal end of the needle is located within the body, and in the injecting position the distal end of the needle protrudes outside of the distal end of the body for injecting medicament into a user.

In some embodiments, the device comprises a mechanism for automatically moving the needle from the pre-use position to the injecting position. The mechanism may be activated by moving the actuation member (e.g. from a protruded position) to the actuation position.

In some embodiments, the actuation member comprises a firing boss for engaging a part of the mechanism to activate the mechanism. The firing boss may comprise one or more protrusions for engaging the part of the mechanism to activate the mechanism. Rotation of the actuation member may move the one or more protrusions from a first position in which the one or more protrusions are not axially aligned with the part of the mechanism to a second position in which the one or more protrusions are axially aligned with the part of the mechanism.

In some embodiments, the mechanism for automatically moving the needle from the pre-use position to the injecting position comprises a spring and a plunger which is biased distally by the spring. When the actuation member is in the actuation position the spring may be released to move the plunger distally from a proximal position to a distal position, thereby causing the needle to move from the pre-use position to the injecting position.

In some embodiments, the plunger comprises proximally-extending flexible clips, and the part of the mechanism which is engageable by the firing boss comprises the proximally-extending flexible clips.

In some embodiments, the medicament delivery device comprises an inner body which contains at least part of the mechanism for automatically moving the needle from the pre-use position to the injecting position.

In some embodiments, the proximally-extending flexible clips are configured to protrude through an opening in the proximal end of the inner body. The proximally-extending flexible clips may engage with the inner body for maintaining the plunger in the proximal position.

In some embodiments, the one or more protrusions of the firing boss are configured to engage with the proximally-extending flexible clips. The one or more protrusions may deflect the proximally-extending clips flexible radially-inwardly for allowing the clips to move distally through the opening, and thereby releasing the spring.

In some embodiments, the device comprises a syringe for containing medicament, the syringe comprises the needle, and the plunger is connected to the syringe for moving the syringe distally. The plunger may be configured to move distally within the syringe for dispensing medicament via the needle.

In some embodiments, the medicament delivery device comprises a container for containing medicament. In some embodiments, the container is a syringe comprising a needle. In some embodiments, the container contains the dose of medicament.

According to a second aspect, a method of using a medicament delivery device is disclosed. The medicament delivery device includes:
  an actuator comprising an actuation member configured to be movable by a user to an actuation position to cause a dose of medicament to be dispensed from the medicament delivery device;
  the actuator being configured to be movable from a deactivated position (or configuration) in which a user is prevented from moving the actuation member to the actuation position to an activated position (or configuration) in which the actuation member is released for movement by a user to the actuation position; and
  a temperature-dependent actuator configured to move the actuator from the deactivated position to the activated position in response to a change in temperature of the temperature-dependent actuator; the method comprising:
  increasing the temperature of the temperature-dependent actuator so as to provide a change in temperature of the temperature-dependent actuator to thereby cause the temperature-dependent actuator to move the actuator from the deactivated position (or configuration) to the activated position (or configuration) in response to the change in temperature of the temperature-dependent actuator; and
  moving the actuation member to the actuation position so as to cause a dose of medicament to be dispensed from the medicament delivery device.

According to a third aspect, a medicament delivery device includes:
  an actuation member configured to be movable by a user to an actuation position to cause a dose of medicament to be dispensed from the medicament delivery device;
  the actuation member being configured to be movable from a deactivated position (or configuration) in which a user is prevented from moving the actuation member to the actuation position to an activated position (or configuration) in which the actuation member is released for movement by a user to the actuation position; and
  a temperature-dependent actuator configured to move the actuation member from the deactivated position (or configuration) to the activated position (or configuration) in response to a change in temperature of the temperature-dependent actuator.

In some embodiments, the actuation member comprises a button configured to be depressible by a user to an actuation position to cause a dose of medicament to be dispensed from the medicament delivery device.

In some embodiments, the actuation member comprises a needle configured to be depressible by a user to an actuation position to cause a dose of medicament to be dispensed from the medicament delivery device.

According to a fourth aspect, a method of using a medicament delivery device includes (i) the medicament delivery device comprising:

an actuation member configured to be movable by a user to an actuation position to cause a dose of medicament to be dispensed from the medicament delivery device;

the actuation member being configured to be movable from a deactivated position in which a user is prevented from moving the actuation member to the actuation position to an activated position in which the actuation member is released for movement by a user to the actuation position; and a temperature-dependent actuator configured to move the actuation member from the deactivated position to the activated position in response to a change in temperature of the temperature-dependent actuator, and (ii) the method comprising:

increasing the temperature of the temperature-dependent actuator so as to provide a change in temperature of the temperature-dependent actuator to thereby cause the temperature-dependent actuator to move the actuation member from the deactivated position to the activated position in response to the change in temperature of the temperature-dependent actuator; and moving the actuation member to the actuation position so as to cause a dose of medicament to be dispensed from the medicament delivery device.

According to a fifth aspect, a medicament delivery device includes:

an actuation member (e.g. a button) configured to be movable (e.g. depressible) by a user to an actuation position to cause a dose of medicament to be dispensed from the medicament delivery device;

a locking member configured to be movable from a locking position, in which the locking member is configured to prevent the actuation member from being moved by a user to the actuation position, to a release position in which the locking member is configured to release the actuation member for movement by a user to the actuation position; and a temperature-dependent actuator configured to move the locking member from the locking position to the release position in response to the change of temperature of the temperature-dependent actuator.

According to a sixth aspect, a method of using a medicament delivery device includes (i) the medicament delivery device comprising:

an actuation member (e.g. a button) configured to be movable (e.g. depressible) by a user to an actuation position to cause a dose of medicament to be dispensed from the medicament delivery device;

a locking member configured to be movable from a locking position, in which the locking member is configured to prevent the actuation member from being moved by a user to the actuation position, to a release position in which the locking member is configured to release the actuation member for movement by a user to the actuation position; and a temperature-dependent actuator configured to move the locking member from the locking position to the release position in response to the change of temperature of the temperature-dependent actuator; and (ii) the method comprising:

increasing the temperature of the temperature-dependent actuator so as to provide a change in temperature of the temperature-dependent actuator to thereby cause the temperature-dependent actuator to move the locking member from the locking position to the release position in response to the change in temperature of the temperature-dependent actuator; and moving the actuation member to the actuation position so as to cause a dose of medicament to be dispensed from the medicament delivery device.

According to a seventh aspect, a medicament delivery device includes:

an actuation member being configured to move:
from an initial position in which the actuation member is prevented from being moved (e.g. from being depressed) by a user to an actuation position to cause a dose of medicament to be dispensed from the medicament delivery device;
to a raised position in which the actuation member is movable (e.g. depressible) by a user to the actuation position to cause a dose of medicament to be dispensed from the medicament delivery device; and a temperature-dependent actuator configured to move the actuation member from the initial position to the raised position in response to the change of temperature of the temperature-dependent actuator.

In some embodiments, the actuation member is movable (e.g. rotatable) by a user from the raised position to a depressible position in which the actuation member is depressible to the actuation position.

In some embodiments, the temperature-dependent actuator is configured to rotate the actuation member as the temperature-dependent actuator moves the actuation member from the initial position to the raised position in order to move the actuation member to a depressible position in which the actuation member is depressible by a user to the actuation position.

According to an eight aspect, a method of using a medicament delivery device includes (i) the medicament delivery device comprising:

an actuation member being configured to move:
from an initial position in which the actuation member is prevented from being moved (e.g. from being depressed) by a user to an actuation position to cause a dose of medicament to be dispensed from the medicament delivery device;
to a raised position in which the actuation member is movable (e.g. depressible) by a user to the actuation position to cause a dose of medicament to be dispensed from the medicament delivery device; and a temperature-dependent actuator configured to move the actuation member from the initial position to the raised position in response to the change of temperature of the temperature-dependent actuator; and (ii) the method comprising:

increasing the temperature of the temperature-dependent actuator so as to provide a change in temperature of the temperature-dependent actuator to thereby cause the temperature-dependent actuator to move the actuation member from the initial position to the raised position in response to the change in temperature of the temperature-dependent actuator; and moving the actuation member to the actuation position so as to cause a dose of medicament to be dispensed from the medicament delivery device.

According to a ninth aspect, a medicament delivery device includes:

an actuator comprising an actuation member configured to be movable by a user to an actuation position to cause a dose of medicament to be dispensed from the medicament delivery device, the actuator being configured to be movable from (i) a deactivated position in which the user is prevented from moving the actuation member to the actuation position to (ii) an activated position in which the actuation member is released for movement by a user to the actuation position; and a temperature-dependent actuator configured to move the actuator from the deactivated position to the activated position in response to a change in temperature of the temperature-dependent actuator.

In some embodiments, the actuation member comprises a button configured to be depressible by the user to the actuation position.

In some embodiments, the actuation member comprises a needle sleeve.

In some embodiments, the actuator comprises a locking member configured to be movable from (i) a locking position in which the locking member is configured to prevent the actuation member from being moved by a user to the actuation position to (ii) a release position in which the locking member is configured to release the actuation member for movement by a user to the actuation position.

In some embodiments, the temperature-dependent actuator is configured to move the locking member from the locking position to the release position in response to the change of temperature of the temperature-dependent actuator.

In some embodiments, the temperature-dependent actuator comprises a bimetallic strip to cause the actuator to rotate from the deactivated position to the activated position in response to a change in temperature of the temperature-dependent actuator.

In some embodiments, the temperature-dependent actuator comprises a piston slidably received within a cylinder.

In some embodiments, the temperature-dependent actuator comprises a phase change actuator comprising a phase change material configured to change phase in response to the change in temperature of the temperature-dependent actuator.

In some embodiments, the temperature-dependent actuator is configured to move the actuation member from an initial position to a raised position in response to the change in temperature of the temperature-dependent actuator.

In some embodiments, when the actuation member is in the raised position, the actuation member is configured to be rotatable to a depressible position in which the actuation member is depressible to the actuation position.

In some embodiments, the actuation member comprises a drive slot and the temperature-dependent actuator comprises a protrusion slidably received within the drive slot for constraining movement of the protrusion with respect to the drive slot.

In some embodiments, the drive slot comprises a circumferentially-extending portion and an axially-extending portion such that, when the actuator is in the deactivated position, the protrusion is received within the circumferentially-extending portion of the drive slot such that the temperature-dependent actuator causes the actuation member to move to the raised position in response to the temperature change of the temperature-dependent actuator.

In some embodiments, the medicament delivery device is configured such that moving the actuation member to the raised position allows the actuation member to rotate to the depressible position to thereby cause the protrusion to enter the axially-extending portion of the drive slot, thereby allowing the actuation member to be depressed by a user from the depressible position to the actuation position.

In some embodiments, the circumferentially-extending portion of the drive slot has an axially-extending component of direction for translating axial movement of the protrusion into rotation of the actuation member to cause the actuation member to rotate to the depressible position.

In some embodiments, the actuation member comprises a guide slot comprising an axially-extending portion, and the medicament delivery device comprises a guide protrusion fixed relative to a body of the device, the guide protrusion located in the guide slot for limiting movement of the actuation member relative to the body, In some embodiments, the medicament delivery device is configured such that when the protrusion is received within the circumferentially-extending portion of the drive slot, the guide protrusion is located in the axially-extending portion of the guide slot for allowing the actuation member to move axially relative to the body as the temperature-dependent actuator moves the actuator from the deactivated position to the activated position.

In some embodiments, the guide slot comprises a circumferentially-extending portion for permitting rotation of the actuation member, the circumferentially-extending portion of the guide slot having a first end connected to the axially-extending portion of the guide slot.

In some embodiments, the medicament delivery device is configured such that when the temperature-dependent actuator moves the actuator from the deactivated position to the activated position, the guide protrusion is caused to travel from the axially-extending portion of the guide slot along the circumferentially-extending portion of the guide slot so as to cause the actuation member to rotate as the actuation member moves to the raised position.

In some embodiments, the medicament delivery device comprises a container for containing medicament. In some cases, the container is a syringe comprising a needle and containing the dose of medicament.

According to a tenth aspect, a medicament delivery device includes:
 a body configured to hold a medicament container;
 a member configured to rotate relative to the body from (i) a first rotational position in which axial movement of the member relative to the body is limited to (ii) a second rotational position in which axial movement of the member is allowed; and
 a temperature-dependent actuator configured to rotate the member from the first rotational position to the second rotational position,
 wherein the medicament delivery device is configured such that when the member is in the second rotational position, the member is axially movable relative to the body along a longitudinal axis of the body to cause a medicament to be dispensed from the medicament container.

In some embodiments, the member comprises a button configured to move between (i) a distal position in which a proximal end of the member extends proximally beyond a proximal end of the body by a first distance and (ii) a proximal position in which the proximal end of the member extends proximally beyond the proximal end of the body by a second distance that is greater than the first distance.

In some embodiments, the medicament delivery device is configured such that when the member is in the second rotational position, the member is movable from the proximal position to the distal position to cause the medicament to be dispensed from the medicament container.

In some embodiments, the member comprises a needle sleeve configured to move between (i) a distal position in which a distal end of the member is distal to a distal end of a needle attached to the medicament container and (ii) a proximal position in which the distal end of the needle is distal to the distal end of member.

In some embodiments, the medicament delivery device is configured such that when the member is in the second rotational position, the member is movable from the distal position to the proximal position to cause the medicament to be dispensed from the medicament container.

In some embodiments, the member is configured to rotate from the first rotational position to the second rotational position without user assistance.

According to an eleventh aspect, a medicament delivery device includes:
   an actuator comprising an actuation member configured to be movable to an actuation position to cause a dose of medicament to be dispensed from the medicament delivery device, the actuator being configured to be movable from (i) a deactivated position in which a movement of the actuation member to the actuation position is limited to (ii) an activated position in which the movement of the actuation member to the actuation position is allowed; and
   a temperature-dependent actuator configured to move the actuator from the deactivated position to the activated position in response to a change in temperature of the temperature-dependent actuator.

In some embodiments, the actuator comprises a locking member configured to be movable from (i) a locking position in which the locking member is configured to prevent the actuation member from being moved by to the actuation position to (ii) a release position in which the locking member is configured to release the actuation member for movement to the actuation position.

According to a twelfth aspect, a method includes:
   increasing a temperature of a temperature-dependent actuator of a medicament delivery device to cause the temperature-dependent actuator to move an actuator of the medicament delivery device from (i) a deactivated position in which a user is prevented from moving the actuation member to an actuation position to (ii) an activation position in which the actuation member is released for movement by a user to the actuation position; and
   after moving the actuator from the deactivated position to the activation position, moving an actuation member of the actuator to the actuation position to cause a dose of a medicament to be dispensed from the medicament delivery device.

In some embodiments, the method includes increasing the temperature of the temperature-dependent actuator to an ambient temperature of the medicament delivery device.

BRIEF DESCRIPTION OF THE DRAWINGS

Embodiments will now be described, by way of example, with reference to the accompanying drawings, in which:

FIG. 1A is a schematic view of a medicament delivery device with a cap attached;

FIG. 1B is a schematic view of the medicament delivery device of FIG. 1A with the cap removed;

FIG. 2A is a schematic view of a medicament delivery device prior to use (i.e. in a pre-use configuration);

FIG. 2B is a schematic view of the device of FIG. 2A with the cap removed;

FIG. 2C is a schematic view of the device of FIG. 2A showing the device placed at an injection site;

FIG. 2D is a schematic view of the device of FIG. 2A with a lock ring of the device having been rotated to allow a button of the device to be depressed by a user;

FIG. 3A is a schematic top view of parts of a medicament delivery device according to a first embodiment, showing an actuator thereof in a deactivated, pre-use, position or configuration;

FIG. 3B is a schematic side cross-sectional view of the device of FIG. 3A taken along section line A-A of FIG. 3A, with the actuator in the deactivated position;

FIG. 3C is a schematic top view of the device of FIG. 3A, showing the actuator in an activated position or configuration in which a button of the device is depressible by a user to an actuation position to cause a dose of medicament to be dispensed from the medicament delivery device;

FIG. 3D is a schematic side cross-sectional view of the device of FIG. 3A taken along section line A-A of FIG. 3A, with the actuator in the activated position;

FIG. 4A is a schematic top view of parts of a medicament delivery device according to a second embodiment, showing an actuator thereof in a deactivated, pre-use, position or configuration;

FIG. 4B is a schematic side cross-sectional view of the device of FIG. 4A taken along section line A-A of FIG. 4A, with the actuator in the deactivated position;

FIG. 4C is a schematic top view of the device of FIG. 4A, showing the actuator in an activated position or configuration in which a needle sleeve of the device is depressible by a user to an actuation position to cause a dose of medicament to be dispensed from the medicament delivery device;

FIG. 4D is a schematic side cross-sectional view of the device of FIG. 4A taken along section line A-A of FIG. 4A, with the actuator in the activated position;

FIG. 5A is a schematic side cross-sectional view of parts of a medicament delivery device according to a third embodiment, showing an actuator thereof in a deactivated, pre-use, position or configuration;

FIG. 5B is a schematic side cross-sectional view of the device of FIG. 5A, showing the actuator in an activated position or configuration in which a button of the device is depressible by a user to an actuation position to cause a dose of medicament to be dispensed from the medicament delivery device;

FIG. 5C is a schematic top view of the device of FIG. 5A, showing a temperature-dependent actuator thereof;

FIG. 7A is a schematic cross-sectional view of parts of a medicament delivery device according to a fifth embodiment, showing an actuator in a deactivation position and with an actuation member thereof in an initial, recessed position;

FIG. 7B is a schematic cross-sectional view of the device of FIG. 7A, showing the actuator moving to an activated position and with the actuation member moving to a raised, or protruded, position;

FIG. 7C is a schematic cross-sectional view of the device of FIG. 7A, showing the actuation member in the raised position, the actuation member rotating to a depressible position in which the actuation member is depressible by a user to an actuation position so as to cause a dose of medicament to be delivered;

FIG. 7D is a schematic cross-sectional view of the device of FIG. 7A, showing the actuator in an activated position with the actuation member in the depressible position, ready to be depressed by a user;

DETAILED DESCRIPTION

Figure 2E:
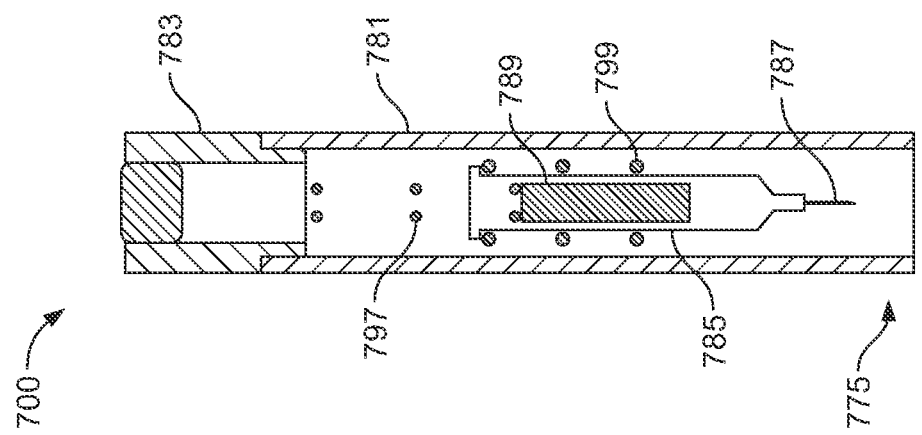
FIG. 2E is a schematic view of the device of FIG. 2A after the button has been depressed and the needle has been caused to move to an exposed position.

A drug delivery device, as described herein, may be configured to inject a medicament into a patient. For example, delivery could be sub-cutaneous, intra-muscular, or intravenous. Such a device could be operated by a patient or a care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an actuation mechanism. Such an actuation mechanism can include one or more of a button, a lever, a needle sleeve, or other actuation component. Actuation of an automated function may be a one-step or multi-step process. That is, a user may need to activate one or more actuation components in order to cause the automated function. For example, in a one-step process, a user may depress a needle sleeve against their body in order to cause injection of a medicament. Other devices may require a multi-step actuation of an automated function. For example, a user may be required to depress a button and retract a needle shield in order to cause injection.

In addition, actuation of one automated function may activate one or more subsequent automated functions, thereby forming an actuation sequence. For example, actuation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11. Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of actuation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following actuation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A to 2G show the sequential steps of operating a medicament injection device 600. As shown in FIG. 2A, the device 700 comprises a body 781, a syringe 785 having a needle 787 and an axially movable plunger 789 for dispensing medicament from the syringe 785. The device comprises a cap 777 which is removably attached to the device 700 and which covers a distal end 775 of the body 781 so as to prevent stick injuries.

As shown in FIGS. 2B-2C, in order to deliver a dose of medicament to an injection site 791, the cap 777 is removed (FIG. 2B) and the device is placed at the injection site 791 (FIG. 2C). An actuator comprising an actuation member 729 in the form of a button 720 is prevented from being depressed by a locking member 783 in the form of a lock ring 783 which is rotatable by a user about a longitudinal axis of the device, by a radially-projecting stop 795. The stop 795 may be provided in the locking member 783 or the stop 795 may be provided on a separate part of the device. As shown in FIG. 2D, in order to allow the button 779 to be depressed by a user, the lock ring 783 is rotated about the longitudinal axis of the device 700 to an actuation member release position (or button release position) in which the stop 795 no longer prevents the button 779 from being depressed by a user.

Figure 2F:
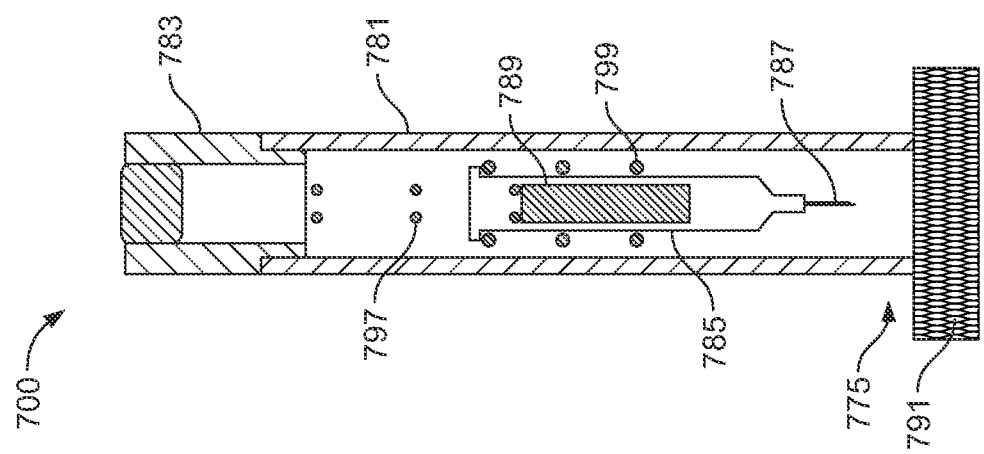
FIG. 2F is a schematic view of the device of FIG. 2A showing the needle retracted within the device after a dose has been delivered.
Figure 2G:
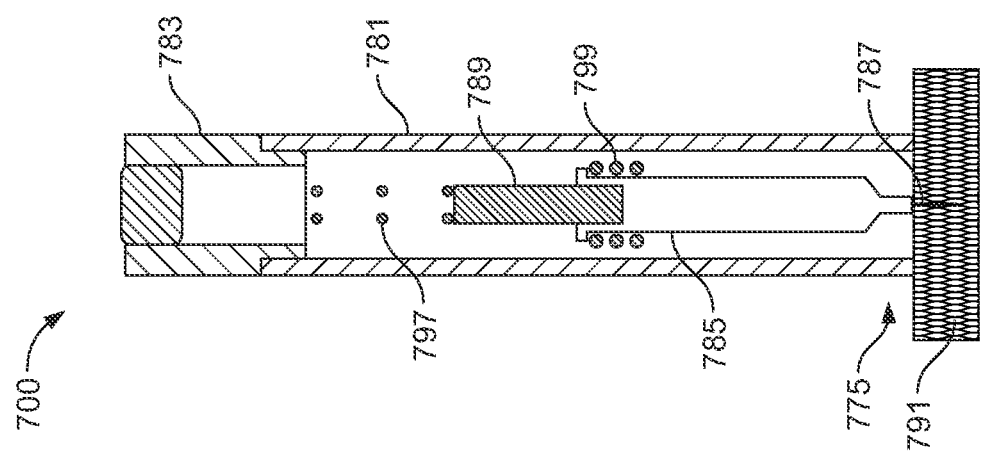
FIG. 2G is a schematic view of the device of FIG. 2A showing the device removed from the injection site after the needle has retracted within the device after delivery of the dose.

Turning now to FIG. 2E, the user then depresses the button 779 from a first position to an actuation position or second position to actuate or trigger a needle mechanism so as to release the syringe 785 for distal axial movement towards the injection site 791 such that the needle 787 moves from a pre-use retracted position to an exposed (or "uncovered") position for delivering medicament to the injection site 791. The syringe 785 is moved distally so as to move the needle 778 thereof to the exposed position under a biasing force provided by a bias 797 in the form of a compression spring 797. Depressing the button 779 also releases the plunger 789 which, biased by the bias 797, moves along the syringe 785 towards the distal end 775 of the device 700 to force medicament within the syringe 785 through the needle 787, thereby delivering a dose of medicament. Thus, the bias 797 causes both the syringe 795 to move distally so as to move the needle 787 thereof to the exposed position and also causes the plunger 789 to move within the syringe 785 so at to cause a dose of medicament within the syringe 785 to be dispensed through the needle 787. As shown in FIG. 2F, once the dose has been delivered, a medicament container bias 799, embodied by a further spring 799, then causes the needle 787 to move axially back to the retracted position, away from the injection site 791 in a proximal direction. As shown in FIG. 2G, the device 700 is then removed from the injection site 791 for later reuse or for disposal.

Turning now to FIGS. 3A to 3D, parts of a first embodiment of medicament delivery device 100 are shown. For ease of illustration, parts of the medicament delivery device 100 are shown, but it will be appreciated that the device 100 of the first embodiment may be provided with one or more of the other parts of the device 700 discussed with reference to FIGS. 2A-2G and in certain embodiments, the device 100 of the first embodiment can be considered to be a modification of the device 700.

In the first embodiment, the device 100 comprises an actuator 101 comprising an actuation member 102 provided in this embodiment as a button 104 which is depressible by a user to an actuation position to cause a dose of medicament to be dispensed from the device 100. In this embodiment, the button 104 is provided at a proximal end of the device 100 so as to be depressible in a distal direction, although the button 104 may be arranged elsewhere in other embodiments.

The actuator 101 is configured to be movable from a deactivated position (shown in FIGS. 3A and 3B) in which a user is prevented from moving the button 104 to the actuation position to an activated position (shown in FIGS. 3C and 3D) in which the button 104 is released (or free) for being moved by a user to the actuation position. The button 104 is movable relative to a fixed part of the device which in this embodiment is a body 119 (or housing 119) of the device.

FIGS. 3A and 3B show the actuator 101 in a deactivated position in which the button 104 is not depressible by a user to the actuation position. As shown in FIG. 3B, in the deactivated position the button 104 is prevented from being depressed by a user to the actuation position for dispensing a dose of medicament by an engagement feature 126 of the button 104 being in abutting engagement with a stop 127 extending from the body 119, the engagement feature 126 and the stop 127 being rotationally aligned in the deactivated position. In this embodiment the engagement feature 126 is provided as a pair of diametrically opposed axially-extending legs 128 of the button 104, although any other suitable feature may instead be used in order to provide the abutting engagement with the stop 127. In this embodiment, each leg 128 is arranged to abuttingly engage with a respective diametrically opposed and radially-inwardly extending stop 127 provided as a projection on the body 119.

FIGS. 3C and 3D show the actuator 101 in an activated position in which the button 104 is depressible by a user to the actuation position. As shown in FIGS. 3C and 3D, in the activated position, the button 104 has rotated such that the engagement feature 126 and the stop 127 are now rotationally misaligned, thereby removing the previous abutting engagement between them. Thus, the button 104 is now released for movement to the actuation position in the sense that the button is now in a depressible position in which the button 104 may be depressed by a user to the actuation position for dispensing a dose of medicament.

A temperature-dependent actuator 103 is configured to move the actuator 101 from the deactivated position to the activated position in response to a change in temperature of the temperature-dependent actuator 103. In this embodiment, the temperature-dependent actuator 103 comprises a bimetallic strip 107 arranged in a spiral so as to cause the actuator 101 (i.e. button 104) to rotate relative to the body 119 from the deactivated position to the activated position in response to a change in temperature of the temperature-dependent actuator 103. The bimetallic strip 107 comprises a first end fixed to the actuation member 102 (i.e. button 104) and a second, opposed end fixed to the body 119.

In this embodiment, the temperature-dependent actuator 103 is configured to move the actuator 101 from the deactivated position to the activated position in response to an increase in temperature of the temperature-dependent actuator 103.

In some embodiments, the temperature-dependent actuator 103 may be configured to move the actuator 101 from the deactivated position to the activated position in response to an increase in temperature of the temperature-dependent actuator 103 of 1, 2, 3, 4, 5, 6, 7, 8, 9, 10, 11, 12, 13, 14, 15, 16, 17, 18, 19, or 20 degrees Celsius or between a range defined by any two of these values.

In some embodiments, the temperature-dependent actuator 103 is configured to move the actuator 101 from the deactivated position to the activated position at or above a predetermined temperature of the temperature-dependent actuator 103, for example at around or above 1, 2, 3, 4, 5, 6, 7, 8, 9, 10, 11, 12, 13, 14, 15, 16, 17, 18, 19, 20, 21, 22, 23, 24 or 25 degrees Celsius.

In some embodiments, the medicament delivery device 100 comprises a visual indicator 129 configured to visually indicate to a user when the actuator 101 is in the activated position. The visual indicator 129 may in some embodiments comprise an indication member 130 and a window or aperture 131, the indication member 130 being movable with respect to the window or aperture 131 such that, in the deactivated position, the indication member 130 is not viewable by a user through the window or aperture 131 and, in the activated position, the indication member 130 is viewable by a user through the window or aperture 131. In the embodiment shown, indication member 130 is operatively coupled to the actuation member 102 (i.e. button 104) so as to move with the actuation member 102 as the actuation member 102 moves to the depressible position.

In order to deliver a dose of medicament, a user first increases the temperature of the device 100. For example, a user may take the device 100 out of cold storage (for example, a fridge or refrigerator) and allow the ambient environment to passively warm the device 100, for example to ambient temperature. Before the temperature of the device 100 is increased, the device 100 is in a pre-use or deactivated configuration in that the actuation member 102 (button 104) is unable to be depressed by the user to the actuation position by way of the blocking engagement between the engagement features 126 of the button 104 and the stops 127 provided in the body 119. Once the device 100 has been sufficiently warmed, the temperature-dependent actuator 103 moves the actuator 101 (e.g. button 104) from its deactivated position to an activated position by rotating the button 104 so as to rotationally misalign the engagement features 126 with their respective stops 127 so as to remove the previous blocking engagement therebetween. Thus, the button 104 is now able to be depressed by a user to the actuation position to thereby cause a dose of medicament to be dispensed.

In this embodiment and in all other embodiments disclosed herein, moving the actuation member 102 to the actuation position causes a dose of medicament to be dispensed from the device 100. This can be achieved in various ways. For example, the actuation member 102 may be directly coupled to a plunger so as to cause the plunger to move within a syringe as the actuation member 102 is moved to the actuation position so as to force medicament through a needle of the syringe in order to deliver the dose of medicament. In other embodiments, the actuation member 102 may be configured to actuate or trigger a mechanism (such as that shown in respect to FIGS. 8A to 8C) to automatically cause a dose of medicament to be delivered when the actuation member 102 is moved to the actuation position. For example, the actuation member 102 may be configured to trigger the release of a plunger biased by a plunger bias so as to cause the plunger to slide within a syringe to cause a dose of medicament to be forced through a needle of the syringe to deliver the dose of medicament to a subject.

In some embodiments the actuation member may be configured to automatically cause a needle of the device to move from a pre-use position in which the needle is covered to an injecting position in which the needled is exposed from a distal end of the device when the actuation member is moved to the actuation position.

In some embodiments, the actuation member 102 (e.g., button 104) can rotate relative to the body 119 from (i) a first rotational position (e.g., FIGS. 3A and 3B) in which axial movement of the actuation member 102 relative to the body 119 is limited to (ii) a second rotational position (e.g., FIGS. 3C and 3D) in which axial movement of the actuation member 102 is allowed. In some examples, when the actuation member 102 is in the second rotational position, the actuation member 102 can distally translate relative to the body 119 along a longitudinal axis of the device 100 from a proximal position (e.g., FIGS. 3A-3D and FIGS. 2A-2D) to a distal position (e.g., FIGS. 2E-2G) to cause a medicament to be dispensed from the device 100. In some examples, the actuation member 102 automatically rotates (e.g., without user assistance) from the first rotational position to the second rotational position by a temperature change of the temperature-dependent actuator 103.

Turning now to FIGS. 4A to 4D, parts of a second embodiment of medicament delivery device 200 are shown. For ease of illustration, parts of the medicament delivery device 200 are shown, but it will be appreciated that the device 200 of the second embodiment may be provided with one or more of the other parts of the device 700 discussed above with reference to FIGS. 2A-2G.

Corresponding features shared between the first and second embodiments share corresponding reference numerals, with those of the second embodiment being increased by 100 as compared to those of the first embodiment.

The medicament delivery device of the second embodiment is substantially the same as that of the first embodiment, with the exception that rather than the actuation member 102 comprising a button 104, in the second embodiment, the actuation member 202 instead comprises a needle sleeve 205. In all other aspects, the first and second embodiments are substantially identical.

The needle sleeve 205 is axially movable in a proximal direction from an extended position in which the needle sleeve 205 extends from a distal end of the device 200 to a retracted, or depressed, position. In the extended position, the needle sleeve 205 may in certain embodiments cover a needle of the device 200 so as to prevent stick injuries. The needle sleeve 205 may in some embodiments comprise an aperture provided in a distal end thereof through which the needle extends when the needle sleeve 205 is in the retracted position. When a user depresses the device 200 against an injection site, the needle sleeve is caused to move proximally from the extended position to the retracted position so as to expose the needle for delivering a dose of medicament through the needle. Movement to the retracted position causes the device 200 to dispense a dose of medicament. Thus, the retracted position can be considered to be an actuation position.

In the same way as in the first embodiment, the actuator 201 is configured to be movable from a deactivated position (shown in FIGS. 4A and 4B), in which a user is prevented from moving the needle sleeve 205 to the actuation position, to an activated position (shown in FIGS. 4C and 4D) in which the needle sleeve 205 is released (or free) for being depressed by a user to the actuation position. The needle sleeve 205 is movable relative to a fixed part of the device which in this embodiment is a body 219 (or housing 219) of the device.

FIG. 4B shows a cross-sectional view taken along section line A-A shown in FIG. 4A. As shown in FIG. 4B, a proximal end of the needle sleeve 205 comprises an engagement feature 226. In the deactivated position, the needle sleeve 205 is prevented from being depressed by a user to the actuation position for dispensing a dose of medicament by the abutting engagement of the engagement feature 226 with a stop 227 extending radially from the body 219, the engagement feature 226 and the stop 227 being rotationally aligned in the deactivated position. In this embodiment the engagement feature 226 is provided as a pair of diametrically opposed axially-extending legs 228 of the needle sleeve 205, although any other suitable feature may instead be used in order to provide the abutting engagements with the stop 227. In this embodiment, each leg 228 is arranged to abuttingly engage with a respective diametrically opposed and radially-inwardly extending stop 227 provided as a projection on the body 219.

FIGS. 4C and 4D show the actuator 201 in an activated position in which the needle sleeve 205 is depressible by a user to the actuation position. As shown in FIGS. 4C and 4D, in the activated position, the needle sleeve 205 has rotated such that the engagement feature 226 and the stop 227 are now rotationally misaligned, thereby removing the previous abutting engagement between them. Thus, the needle sleeve 205 is now released for movement to the actuation position in the sense that the needle sleeve 205 is now in a depressible position in which the needle sleeve 205 may be depressed by a user to the actuation position for dispensing a dose of medicament.

A temperature-dependent actuator 203 is configured to move the actuator 201 from the deactivated position to the activated position in response to a change in temperature of the temperature-dependent actuator 203. In this embodiment, the temperature-dependent actuator 203 comprises a bimetallic strip 207 arranged in a spiral so as to cause the actuator 201 (i.e. needle sleeve 205) to rotate relative to the body 219 from the deactivated position to the activated position in response to a change in temperature of the temperature-dependent actuator 203. The bimetallic strip 207 comprises a first end fixed to the actuation member 202 (i.e. needle sleeve 205) and a second, opposed end fixed to the body 219.

In this embodiment, the temperature-dependent actuator 203 is configured to move the needle sleeve 205 from the deactivated position to the activated position in response to an increase in temperature of the temperature-dependent actuator 203.

In some embodiments, the temperature-dependent actuator 203 may be configured to move the needle sleeve 205 from the deactivated position to the activated position in response to an increase in temperature of the temperature-dependent actuator 203 of 1, 2, 3, 4, 5, 6, 7, 8, 9, 10, 11, 12, 13, 14, 15, 16, 17, 18, 19, or 20 degrees Celsius or between a range defined by any two of these values.

In some embodiments, the temperature-dependent actuator 203 is configured to move the actuator 201 from the deactivated position to the activated position at or above a predetermined temperature of the temperature-dependent actuator 103, for example at around or above 1, 2, 3, 4, 5, 6, 7, 8, 9, 10, 11, 12, 13, 14, 15, 16, 17, 18, 19, 20, 21, 22, 23, 24 or 25 degrees Celsius.

In some embodiments, the medicament delivery device 200 comprises a visual indicator 229 configured to visually indicate to a user when the actuator 201 is in the activated position. The visual indicator 229 may in some embodiments comprise an indication member 230 and a window or aperture 231, the indication member 230 being movable with respect to the window or aperture 231 such that, in the deactivated position, the indication member 230 is not viewable by a user through the window or aperture 231 and, in the activated position, the indication member 230 is viewable by a user through the window or aperture 231. In the embodiment shown, the indication member 230 is operatively coupled to the actuation member 202 (i.e. needle sleeve 205) so as to move with the actuation member 202 as the actuation member 202 moves to the depressible position.

In order to deliver a dose of medicament, a user first increases the temperature of the device 200. For example, a user may take the device 200 out of cold storage (for example, a fridge or refrigerator) and allow the ambient environment to passively warm the device, for example to ambient temperature. Before the temperature of the device is increased, the device 200 is in a pre-use or deactivated configuration in that the needle sleeve 205 is unable to be depressed by the user to the actuation position by way of the blocking engagement between the engagement features 226 of the needle sleeve 205 and the stops 227 provided in the body 219, preventing the needle sleeve 205 from moving proximally from the extended position to the actuation position. Once the device 200 has been sufficiently warmed, the temperature-dependent actuator 203 moves the actuator 201 from its deactivated position to an activated position by rotating the needle sleeve 205 so as to rotationally misalign the engagement feature 226 with its respective stop 227 so as to remove the previous blocking engagement therebetween in the deactivated position. Thus, the needle sleeve 205 is now able to be depressed to the actuation position to thereby cause a dose of medicament to be dispensed.

In some embodiments, the actuation member 202 (e.g., needle sleeve 205) can rotate relative to the body 219 from (i) a first rotational position (e.g., FIGS. 4A and 4B) in which axial movement of the actuation member 202 relative to the body 219 is limited to (ii) a second rotational position (e.g., FIGS. 4C and 4D) in which axial movement of the actuation member 202 is allowed. In some examples, when the actuation member 202 is in the second rotational position, the actuation member 202 can proximally translate relative to the body 219 along a longitudinal axis of the device 200 from (i) a distal position in which a distal end of the actuation member 202 is distal to a distal end of a needle attached to a syringe of the device 200 and (ii) a proximal position in which the distal end of the needle is distal to the distal end of actuation member 202. In some examples, the proximal position is a position which is more proximal than the distal position. In some examples, moving the actuation member 202 from the distal position to the proximal position causes a medicament to be dispensed from the device 200. In some examples, the actuation member 202 automatically rotates (e.g., without user assistance) from the first rotational position to the second rotational position by a temperature change of the temperature-dependent actuator 203.

Turning now to FIGS. 5A to 5C, parts of a third embodiment of medicament delivery device 300 are shown. For ease of illustration, parts of the medicament delivery device 300 are shown, but it will be appreciated that the device 300 of the third embodiment may be provided with one or more of the other parts of the device 700 discussed with reference to FIGS. 2A-2G.

Corresponding features shared between the first and third embodiments share corresponding reference numerals, with those of the third embodiment being increased by 200 as compared to those of the first embodiment.

In the device 300 of the third embodiment, the actuator 301 comprises a locking member 306 and an actuation member 302. The locking member 306 is movable from a locking position (FIG. 5A) to a release position (FIG. 5B). The locking position corresponds with a deactivated position of the actuator 301 and the release position corresponds with an activated position of the actuator 301.

In the locking position, shown in FIG. 5A, the locking member 306 (in this embodiment, provided as a lock ring 306) prevents the actuation member 302 from being moved to the actuation position by a user. In this embodiment, the actuation member 302 comprises a button 304 which is prevented from being depressed to the actuation position by way of blocking engagement between an engagement feature 326, here provided as an axially-extending leg 328 provided on the button 304, and a stop 327 fixed to a body (e.g. housing) of the device 300. In the locking position, the engagement feature 326 abuts against the stop 327 thereby preventing the button 304 from being depressed by a user in an axial direction to the actuation position.

In the release position, shown in FIG. 5B, the actuation member 302 is released by the locking member 306 for movement by a user to the actuation position. In this embodiment the locking member 306 is rotatable between the locking position and the release position and the button 304 is rotationally coupled to the locking member 306 so as to rotate with the locking member 306 upon rotation of the locking member 306 between the locking position and the release position. As can be seen in FIG. 5B, in the release position, the axially-extending leg 328 of the button 304 is removed from blocking engagement with the stop 327 as the axially-extending leg 328 is rotationally misaligned with the stop 327. As the axially-extending leg 332 is rotationally misaligned with the stop 327, the button 304 is now depressible by a user to the actuation position for causing a dose of medicament to be dispensed from the device 300.

The device 300 further comprises a temperature-dependent actuator 303 configured to move the locking member 306 from the locking position to the release position in response to a change of temperature of the temperature-dependent actuator 303. In this embodiment, the temperature-dependent actuator 303 comprises a bimetallic strip 307 (best seen in FIG. 5C) arranged in a spiral so as to cause the locking member 306 to rotate relative to a body 319 of the device 300 from the locking position (corresponding to a deactivated position) to the release position (corresponding to an activated position) in response to a change in temperature of the temperature-dependent actuator 303. The bimetallic strip 307 comprises a first end fixed to an axially-extending shaft 334 provided on the locking member 306 and a second, opposed end fixed to the body 319.

In this embodiment, the temperature-dependent actuator 303 is configured to move (i.e. rotate) the locking member 306 from the locking position to the release position in response to an increase in temperature of the temperature-dependent actuator 303.

In some embodiments, the temperature-dependent actuator 303 may be configured to move the locking member 306 from the locking position to the release position in response to an increase in temperature of the temperature-dependent actuator 303 of 1, 2, 3, 4, 5, 6, 7, 8, 9, 10, 11, 12, 13, 14, 15, 16, 17, 18, 19, or 20 degrees Celsius or between a range defined by any two of these values.

In some embodiments, the temperature-dependent actuator 303 is configured to move the locking member 306 from the deactivated position to the activated position at or above a predetermined temperature of the temperature-dependent actuator 303, for example at around or above 1, 2, 3, 4, 5, 6, 7, 8, 9, 10, 11, 12, 13, 14, 15, 16, 17, 18, 19, 20, 21, 22, 23, 24 or 25 degrees Celsius.

In order to deliver a dose of medicament, a user first increases the temperature of the device 300. For example, a user may take the device 300 out of cold storage (for example, a fridge or refrigerator) and allow the ambient environment to passively warm the device, for example to ambient temperature. Before the temperature of the device 300 is increased, the device 300 is in a pre-use deactivated configuration in that the button 304 is unable to be depressed by the user to the actuation position by way of the blocking engagement between the engagement feature 326 of the button 304 and the stop 327 provided on the body 319. Once the device 300 has been sufficiently warmed, the temperature-dependent actuator 303 rotates the locking member 306 of the actuator 301 from its locking position to its release position. As the locking member 306 rotates to the release position, the button 304 rotates therewith, causing the engagement feature 326 of the button 304 to become rotationally misaligned with its respective stop 327 so as to remove the previous blocking engagement therebetween. Thus, the button 304 is now able to be depressed to the actuation position to thereby cause a dose of medicament to be dispensed.

In some embodiments, the locking member 306 (e.g., lock ring 306) can rotate relative to the body 319 from (i) a first rotational position (e.g., FIG. 5A) in which distal movement of an actuation member 302 (e.g., button 304) relative to the body 319 is limited to (ii) a second rotational position (e.g., FIG. 5B) in which distal movement of the actuation member 302 is allowed. In some examples, when the locking member 306 is in the second rotational position, the actuation member 302 can distally translate relative to the body 319 along a longitudinal axis of the device 300 from a proximal position to a distal position to cause a medicament to be dispensed from the device 300. In some examples, the locking member 306 automatically rotates (e.g., without user assistance) from the first rotational position to the second rotational position by a temperature change of the temperature-dependent actuator 303.

While in the first, second and third embodiments described above, the temperature-dependent actuators 103; 203; and/or 303 comprise a bimetallic strip 107; 207; and/or 307, other temperature-dependent actuators may instead be used. For example, in some embodiments, the temperature-dependent actuator may comprise a wax motor. In some embodiments, the temperature-dependent actuator may comprise a cylinder and a piston slidably received in the piston. The cylinder may contain a mass of material having a temperature-variable volume so as to drive the piston according to the change in temperature of the material. The mass of material may be provided as a solid, liquid or as a gas. In certain embodiments, the material may be a wax. The material may be a phase-change material which changes phase as its temperature increases, for example from a solid to liquid or from a liquid to a gas. The phase change material may be selected so as to change phase above a predetermined temperature or within a predetermined temperature range.

Turning now to FIGS. 6A to 6D, parts of a fourth embodiment of medicament delivery device 400 are shown. For ease of illustration, parts of the medicament delivery device 400 are shown, but it will be appreciated that the device 400 of the fourth embodiment may be provided with one or more of the other parts of the device 700 discussed with reference to FIGS. 2A-2G.

Corresponding features shared between the first and fourth embodiments share corresponding reference numerals, with those of the fourth embodiment being increased by 300 as compared to those of the first embodiment.

In FIGS. 6A to 6D, the actuator 401 comprises an actuation member 402 provided in the form of a button 404. The actuation member comprises a drive slot 413. A temperature-dependent actuator 403 comprises a protrusion 414. The protrusion 414 is located in the drive slot 413 for constraining movement of the protrusion 414 relative to the actuation member 402. The drive slot 413 comprises a circumferentially-extending portion 415 comprising an abutment surface 435. The abutment surface 435 is formed by part of the surface of the drive slot 413 in the circumferentially-extending portion 415.

The temperature-dependent actuator 403 causes the protrusion 414 to move axially in a proximal direction in response to a change in temperature of the temperature-dependent actuator 403 so as to drive the actuation member 402 (here, button 404) from a recessed position (shown in FIG. 6A) in which the actuation member 402 is recessed within a body 419 of the device 400 so as not to be movable by a user to the activation position (shown in FIG. 6B) in which the actuation member 402 extends axially from a proximal end of the device 400 and is movable by a user to the actuation position. Thus, the recessed position corresponds to a deactivated position of the actuator 401 (i.e. the actuation member 402) and the raised position corresponds to an activated position of the actuator 401.

In the embodiment shown, the temperature-dependent actuator 403 comprises a piston 408 arranged within a cylinder 409, the cylinder 409 comprising a contained mass of material having a temperature-variable volume. The protrusion 414 is coupled to the piston 408 such that the piston 408 drives the protrusion 414 against the abutment surface 435 in response to a change in temperature of the temperature-dependent actuator 403 thereby causing the actuation member 402 to move to the raised position. In this embodiment, the temperature-dependent actuator 403 moves the actuation member 402 to the raised position in response to an increase in temperature of the material within the cylinder 409. The material may be a wax or a phase change material for example.

In some embodiments, the temperature-dependent actuator 403 may be configured to move the actuator 401 from the deactivated position to the activated position in response to an increase in temperature of the temperature-dependent actuator 403 of 1, 2, 3, 4, 5, 6, 7, 8, 9, 10, 11, 12, 13, 14, 15, 16, 17, 18, 19, or 20 degrees Celsius or between a range defined by any two of these values.

In some embodiments, the temperature-dependent actuator 403 is configured to move the actuator 401 from the deactivated position to the activated position at or above a predetermined temperature of the temperature-dependent actuator 403, for example at around or above 1, 2, 3, 4, 5, 6, 7, 8, 9, 10, 11, 12, 13, 14, 15, 16, 17, 18, 19, 20, 21, 22, 23, 24 or 25 degrees Celsius.

Figure 6A:
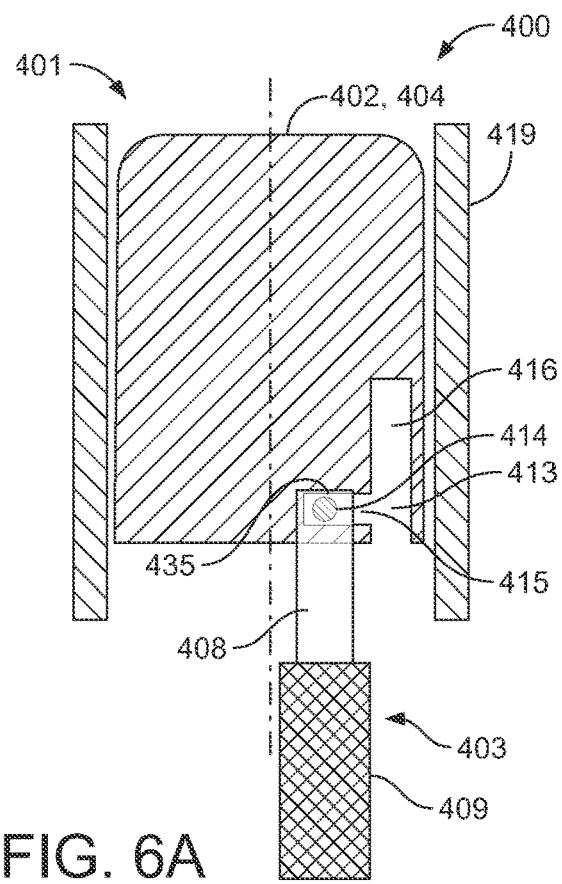
FIG. 6A is a schematic cross-sectional view of parts of a medicament delivery device according to a fourth embodiment, showing an actuator in a deactivation position and with an actuation member thereof in an initial, recessed position.
Figure 6B:
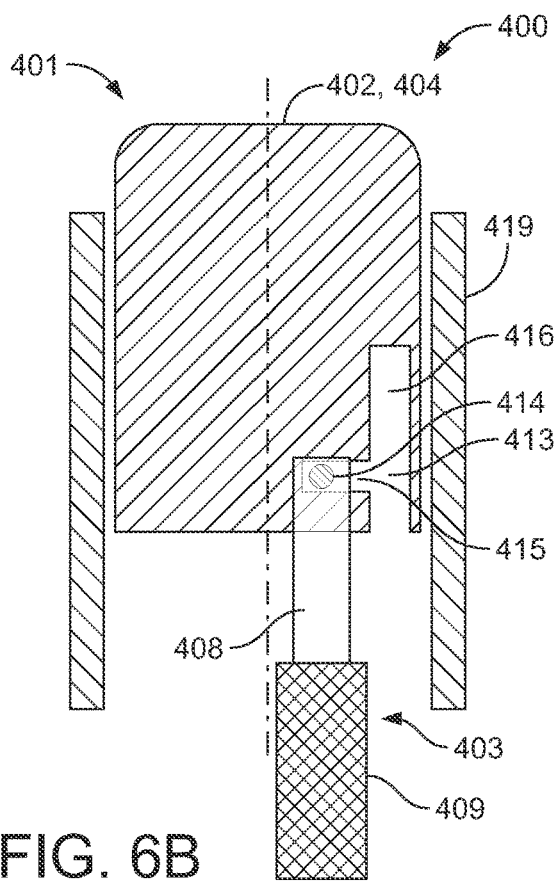
FIG. 6B is a schematic cross-sectional view of the device of FIG. 6A, showing the actuator in an activated position and with the actuation member in a raised, or protruded, position, so as to be rotatable by a user.

As the volume of the material within the cylinder 409 increases, the protrusion 414 engages the abutment surface 435, thereby causing the actuation member 402 (button 404) to move from the initial, recessed position to the raised (or protruded) position. FIG. 6A shows an example of the actuation member 402 in the initial position. FIG. 6B shows an example of the actuation member in the protruded position.

The circumferentially-extending portion 415 of the drive slot 413 is orthogonal or substantially orthogonal to a longitudinal axis of the body 419.

The drive slot 413 has an axially-extending portion 416 connected to the circumferentially-extending portion 415. When the actuation member 402 is in the raised (or protruded) position, the actuation member 402 can be gripped by a user and rotated by the user relative to the body 419 to move the protrusion 414 from the circumferentially-extending portion 415 of the drive slot 413 to the axially-extending portion 416 of the drive slot 413.

Figure 6C:
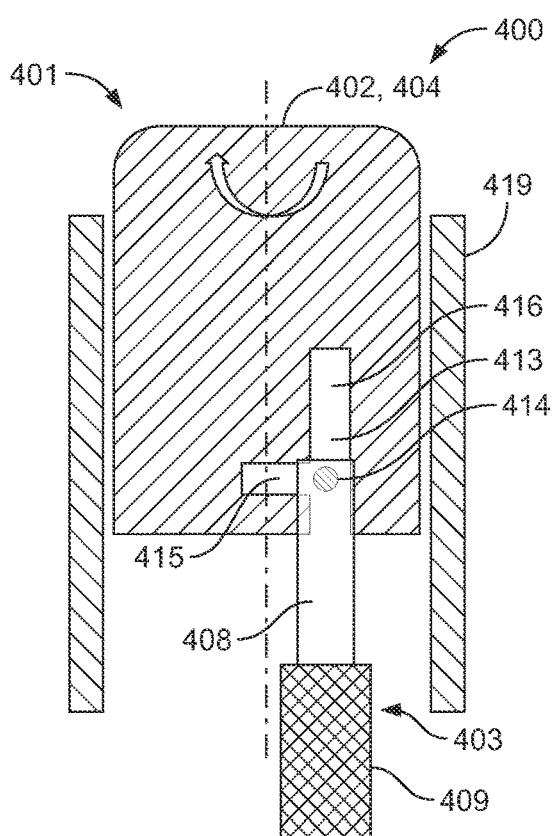
FIG. 6C is a schematic cross-sectional view of the device of FIG. 6A, showing the actuation member having been rotated by a user to a depressible position in which the actuation member is depressible by a user to an actuation position so as to cause a dose of medicament to be delivered.

FIG. 6C shows an example of the actuation member 402 after it has been rotated by a user. The axially-extending portion 416 is parallel to or substantially parallel to a longitudinal axis of the body 419.

Figure 6D:
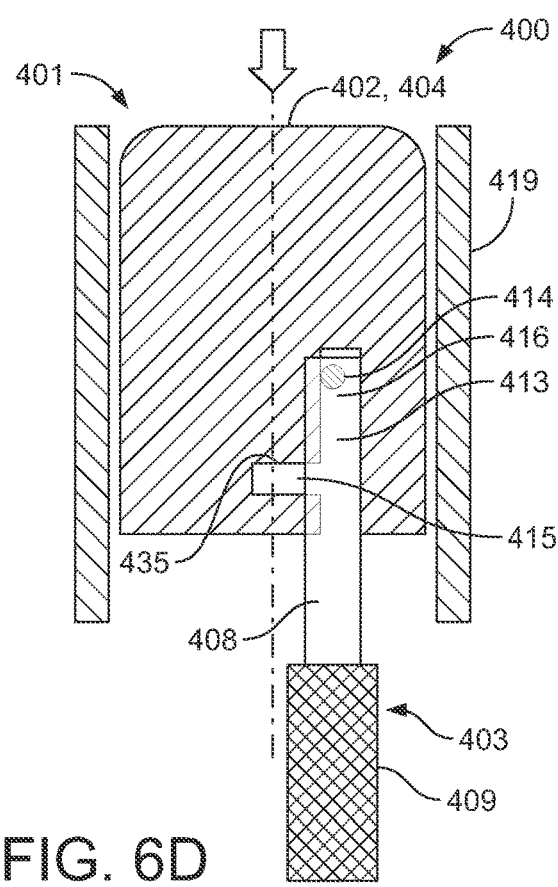
FIG. 6D is a schematic cross-sectional view of the device of FIG. 6A, showing the actuation member being depressed by a user to the actuation position so as to cause a dose of medicament to be delivered.

When the protrusion 414 is located in the axially-extended portion 416 of the drive slot, the actuation member 402 is depressible by a user from the raised position to the actuation position as shown, for example in FIG. 6D. The protrusion 414 travels along the axially-extending portion 416 of the drive slot 413 when the actuation member 402 is depressed from the raised position to the actuation position.

In order to deliver a dose of medicament, a user first increases the temperature of the device 400. For example, a user may take the device 400 out of cold storage (for example, a fridge or refrigerator) and allow the ambient environment to passively warm the device 400, for example to ambient temperature. Before the temperature of the device 400 is increased, the actuator 401 (i.e. actuation member 402) is in a pre-use or deactivated position in that the actuation member 402 (button 404) is unable to be moved by the user to the actuation position as the actuation member 402 is recessed within the body 419 of the device 400. As the temperature of the temperature-dependent actuator 403 increases, the piston 408 drives the protrusion 414 against the abutment surface 435 so as to drive the actuation member 402 axially in a proximal direction from the initial, recessed position to the protruded position. Thus the device 400 presents the actuation member 402 to a user for movement to a position in which the actuation member 402 is depressible by the user to the actuation position.

When the actuation member 402 is in the protruded position, a user grips the actuation member 402 and rotates the actuation member 402 relative to the body 419. The rotation moves the protrusion 414 from the circumferentially-extending portion of the drive slot 413 to the axially-extending portion 416 of the drive slot 413.

A user can then move (i.e. depress) the actuation member 402 distally relative to the body 419 from the protruded position to the actuation position. If the actuation member 402 comprises a button 404 then a user presses the button 404 towards the body 419 to move the actuation member 402 distally relative to the body 419.

Turning now to FIGS. 7A to 7E, parts of a fifth embodiment of medicament delivery device 500 are shown. For ease of illustration, parts of the medicament delivery device 500 are shown, but it will be appreciated that the device 500 of the fifth embodiment may be provided with one or more of the other parts of the device 700 discussed with reference to FIGS. 2A-2G.

Corresponding features shared between the first and fifth embodiments share corresponding reference numerals, with those of the fifth embodiment being increased by 400 as compared to those of the first embodiment.

Figure 7E:
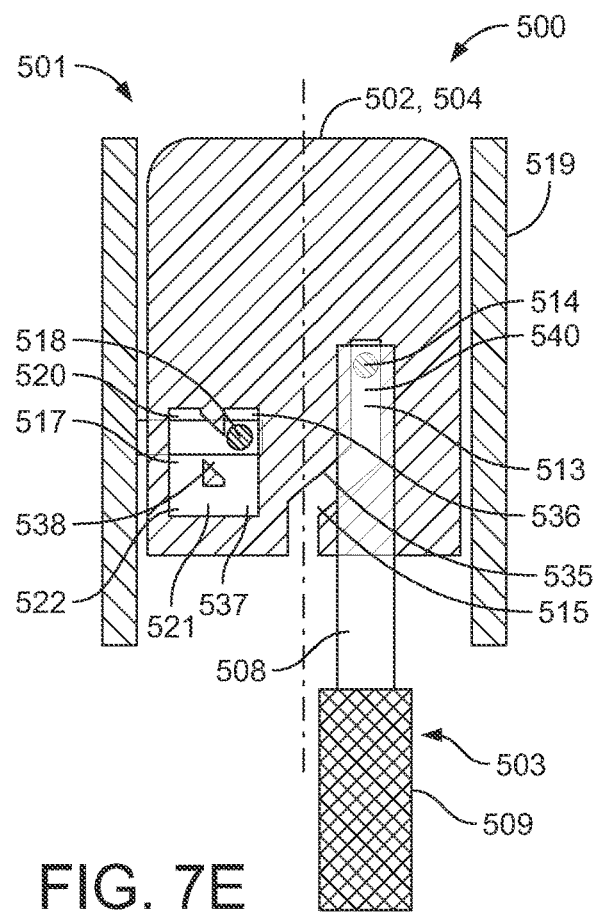
FIG. 7E is a schematic cross-sectional view of the device of FIG. 7A, showing the actuation member being depressed by a user to the actuation position so as to cause a dose of medicament to be delivered.

In FIGS. 7A to 7E, the actuator 501 comprises an actuation member 502 provided in the form of a button 504. The actuation member 502 comprises a drive slot 513. A temperature-dependent actuator 503 comprises a protrusion 514. The protrusion 514 is located in the drive slot 513 for constraining movement of the protrusion 514 relative to the actuation member 502. The drive slot 513 comprises a circumferentially-extending portion 515 comprising an abutment surface 535. The abutment surface 535 is formed by part of the surface of the drive slot 513 in the circumferentially-extending portion 515. The drive slot 513 comprises a first axially-extending portion 539 connected to the circumferentially-extending portion of the drive slot 534 at a first end thereof. The protrusion 514 is located in the first axially-extending portion 514 when the actuation member 502 is in the deactivation position, as shown in FIG. 7A, in which the actuation member 502 is in an initial, recessed position (corresponding to a deactivated position of the actuator 501) within a body 519 of the device. The first axially-extending portion 536 is parallel to or substantially parallel to a longitudinal axis of the body 519. In another embodiment, the drive slot does not have a first axially-extending portion 539 and the protrusion 514 is located in the circumferentially-extending portion 515 when the actuation member 502 is in the deactivated position.

The circumferentially-extending portion 515 of the drive slot 513 has an axially-extending component of direction for translating axial movement of the protrusion 514 into rotation of the actuation member 502 relative to the body 519.

The drive slot 513 has a second axially-extending portion 540 connected to the circumferentially-extending portion 515. The second axially-extending portion 540 is connected to the circumferentially-extending portion 515 at the opposite end to the first axially-extending portion 539. The second axially-extending portion 540 is parallel to or substantially parallel to the longitudinal axis of the body 519.

A temperature-dependent actuator 503 causes the protrusion 514 to move axially in a proximal direction in response to a change in temperature of the temperature-dependent actuator 503 so as to drive the actuation member 502 (here, button 504) from a recessed position (shown in FIG. 7A) in which the actuation member 502 is recessed within a body 519 of the device 500 so as not to be movable by a user to the actuation position to a raised position (shown in FIG. 7E) in which the actuation member 502 extends axially from a proximal end of the device 500 and is depressible by a user to the actuation position. Thus, the recessed position corresponds to a deactivated position of the actuator 501 (i.e. the actuation member 502) and the raised position corresponds to an activated position of the actuator 501.

In the embodiment shown, the temperature-dependent actuator 503 comprises a piston 508 arranged within a cylinder 509, the cylinder 509 comprising a contained mass of material having a temperature-variable volume. The protrusion 514 is coupled to the piston 508 such that the piston 508 drives the protrusion 514 against the abutment surface 535 of the circumferentially-extending portion 515 of the drive slot 513, thereby causing the actuation member 502 to move to the raised position, in response to a change in temperature of the temperature-dependent actuator 503. In this embodiment, the temperature-dependent actuator 503 moves the actuation member 502 to the raised position in response to an increase in temperature of the material within the cylinder 509. The material may be a wax or a phase change material for example.

In some embodiments, the temperature-dependent actuator 503 may be configured to move the actuator 501 from the deactivated position to the activated position in response to an increase in temperature of the temperature-dependent actuator 503 of 1, 2, 3, 4, 5, 6, 7, 8, 9, 10, 11, 12, 13, 14, 15, 16, 17, 18, 19, or 20 degrees Celsius or between a range defined by any two of these values.

In some embodiments, the temperature-dependent actuator 503 is configured to move the actuator 501 from the deactivated position to the activated position at or above a predetermined temperature of the temperature-dependent actuator 503, for example at around or above 1, 2, 3, 4, 5, 6, 7, 8, 9, 10, 11, 12, 13, 14, 15, 16, 17, 18, 19, 20, 21, 22, 23, 24 or 25 degrees Celsius.

As the volume of the material within the cylinder 509 increases as the temperature increases, the protrusion 514 engages the abutment surface 535, thereby causing the actuation member 502 (button 504) to move from the initial, recessed position to the raised (or protruded) position. FIG. 7A shows an example of the actuation member 502 in the initial position. FIG. 7C shows an example of the actuation member in the protruded position.

As the circumferentially-extending portion 515 of the drive slot 513 has an axially-extending component, as the protrusion 514 moves axially and along the circumferentially-extending portion 515 of the drive slot 513, the engagement surface 535 resolves a component of this axial movement into rotation of the actuation member 502 relative to the body 519.

When the actuation member 502 is in the protruded position and has been rotated relative to the body 519, the protrusion 514 is moved to the second axially-extending portion 540 of the drive slot. FIG. 7D shows an example of the actuation member 502 after it has been rotated.

When the protrusion 514 is located in the second axially-extended portion 540 of the drive slot 513, the actuation member 502 can be depressed by a user from the protruded position to the actuation position as shown, for example in FIG. 7E. The protrusion 514 travels along the second axially-extending portion 540 of the drive slot 513 when the actuation member 502 is depressed from the raised position to the actuation position.

The actuation member 502 comprises a guide slot 517. The medicament delivery device 500 comprises a guide protrusion 518 which is fixed relative to the body 519. The guide protrusion 518 may be provided on an inner surface of the body 519, or a surface of an internal component, for example. The guide protrusion 518 is located in the guide slot 517 for constraining movement of the actuation member 502 relative to the body 519.

The guide slot 517 has a first axially-extending portion 520. When the protrusion 514 engages the abutment surface 535, the guide protrusion 518 is located in the first axially-extending portion 520 of the guide slot 517 for allowing the actuation member 502 to move axially relative to the body 519 when the temperature-dependent actuator increases in temperature. The guide protrusion 518 and the first axially-extending portion 520 of the guide slot 517 constrain the rotational movement of the actuation member 502 relative to the body 519. In FIGS. 7A to 7E the first axially-extending portion 520 of the guide slot 517 is parallel to the longitudinal axis of the body 519. In another embodiment, the first axially-extending portion 520 may have a circumferential component of direction so that the first axially-extending portion 520 is at an angle relative to the longitudinal axis of the body 519.

The guide slot 517 has a circumferential-extending portion 521 for permitting rotation of the actuation member 502 relative to the body 519. The circumferentially-extending portion of the guide slot 517 has a first end 522 connected to the first axially-extending portion 520 of the guide slot 517. When the actuation member 502 is caused to move to the activation position (i.e. the raised or protruded position shown in FIG. 7C) by way of the temperature-dependent actuator 503, the guide protrusion 518 travels from the first axially-extending portion 520 of the guide slot 517 to the circumferentially-extending portion 521 of the guide slot 517. The protrusion 518 and the circumferentially-extending portion 521 of the guide slot 517 constrain the axial movement of the actuation member 502 relative to the body 519. In FIGS. 7A to 7E the circumferentially-extending portion 521 is orthogonal or substantially orthogonal to the longitudinal axis of the body 519.

When the guide protrusion 518 is in the circumferentially-extending portion 521 of the guide slot 517, the protrusion 514 is in the circumferentially-extending portion 515 of the drive slot 513. Proximal movement of the actuation member 502 towards the raised position is translated into rotation of the actuation member 502 relative to the body 519. Rotation of the actuation member 502 moves the protrusion 514 into the second axially-extending portion 540 of the drive slot 513 as shown, for example, in FIG. 7D. As noted, the protrusion 514 and the circumferentially-extending portion 521 of the guide slot 517 constrain the axial movement of the actuation member 502 relative to the body 519.

The guide slot 517 has a second axially-extending portion 536 connected to a second end 537 of the circumferentially-extending portion 521 of the guide slot 517 for allowing the actuation member 502 to move distally relative to the body 519. The protrusion 518 and the second axially-extending portion 536 of the guide slot 517 constrain the rotational movement of the actuation member 502 relative to the body 519. The second axially-extending portion 536 of the guide slot 517 is parallel to or substantially parallel to the longitudinal axis of the body 519.

When the actuation member 502 rotates relative to the body 519, the guide protrusion 518 travels along the circumferentially-extending portion 521 of the guide slot 517 to the second axially-extending portion 536 of the guide slot 517. The actuation member 502 can then be moved distally relative to the body 519 (e.g. by a user, i.e. depressed) when the guide protrusion 518 is in the second axially-extending portion 536 of the guide slot 517, as the actuation member 502 moves from the protruded position to the actuation position as shown, for example, in FIG. 7E.

When the actuation member 502 moves from the protruded position to the actuation position, the protrusion 514 travels in the second axially-extending portion 540 of the drive slot 513, and the guide protrusion 518 travels in the second axially-extending portion 536 of the guide slot 517.

The guide slot 517 has a diagonally-extending portion 538 connecting the second axially-extending portion 536 to the first axially-extending portion 520 for allowing the guide protrusion 518 to return to the first axially-extending portion 520 and the actuation member 502 to return to the initial position shown in FIG. 7A.

If the temperature-dependent actuator 503 cools while the protrusion 518 is in the second axially-extending portion 540 of the guide slot 517 and before the actuation member 502 has been moved by a user from the protruded position to the actuation position, the temperature-dependent actuator 503 returns the actuation member 502 to the initial position (FIG. 7A) by way of the guide protrusion 518 travelling along the diagonally extending portion 538. A biasing means configured to rotate the actuation member 502 may assist or cause the guide protrusion 518 to enter diagonally extending portion 538. Thus, the guide protrusion 518 travels from the second axially-extending portion 536 of the guide slot 517 to the first axially-extending portion 520 of the guide slot 517 along the diagonally-extending portion 538.

In a pre-use configuration of the device 500 (FIG. 7A), the actuator 501 in a deactivated position in that that the actuation member 502 is not movable by a user to the actuation position as it is recessed within the body 519. The protrusion 514 is located in the first axially-extending portion 539 of the drive slot 513. The guide protrusion 518 is located in the first axially-extending portion 520 of the guide slot.

In order to deliver a dose of medicament, a user first increases the temperature of the device 500. For example, a user may take the device 500 out of cold storage (for example, a fridge or refrigerator) and allow the ambient environment to passively warm the device 500, for example to ambient temperature. As the temperature of the temperature-dependent actuator 503 increases, the piston 508 is caused to extend by way of the volume of the material within the cylinder 509 increasing in response to the increase in temperature. The piston 508 travels along the first axially-extending portion 539 of the drive slot 513 and enters the circumferentially-extending portion 515. As the piston extends, the piston 508 then drives the protrusion 514 against the abutment surface 535 (FIG. 7B) so as to drive the actuation member 502 axially in a proximal direction from the initial, recessed position to the protruded position (FIG. 7D). Rotation of the actuation member 502 is initially constrained by the guide protrusion 518 as the guide protrusion 518 travels along the first axially-extending portion 520 of the guide slot 517 until the guide protrusion 518 enters the circumferentially-extending portion 521 of the guide slot 517 at which point the actuation member 502 is in the protruded position.

Further extension of the piston 508 then causes protrusion 514 to travel further along the circumferentially-extending portion of the 515 of the drive slot 513, thereby causing the actuation member 502 to rotate and the guide protrusion 518 to move along the circumferentially-extending portion 521 of the guide slot 517 until the piston 508 is fully extended, causing the protrusion 514 to enter the second axially-extending portion 540 of the drive slot 513 and the guide protrusion 518 to enter the second axially-extending portion 536 of the guide slot 517. Further proximal axial movement of the actuation member 502 as the actuation member 502 rotates is prevented by the engagement of the guide protrusion 518 with the circumferentially-extending portion 521 of the guide slot 517.

When the piston 508 is fully extended, the actuation member 502 is in a depressible position, as shown in FIG. 7D, in which the actuation member 502 is depressible to the actuation position by a user. Thus, in this embodiment, the user does not rotate the actuation member 502 from the release position to the depressible position as the rotation is instead effectuated or caused by the temperature-dependent actuator 503.

As shown in FIG. 7E, a user can then move (i.e. depress) the actuation member 502 distally relative to the body 519 from the protruded position to the actuation position in order to deliver a dose of medicament. If the actuation member 502 comprises a button 504 then a user presses the button 504 towards the body 519 to move the actuation member 502 distally relative to the body 519. When the actuation member 502 is moved by a user to the actuation position, the protrusion 514 is caused to move along the second axially-extending portion 540 of the drive slot 513 and the guide protrusion 518 is caused to moved along the second axially-extending portion 536 of the guide slot 517.

If the actuation member 502 is not depressed by a user when the actuation member 502 is in the depressible position but the device 500 is instead cooled, the temperature-dependent actuation 503 cools and the piston 508 retracts, thereby causing the protrusion 514 to travel back down the circumferentially-extending portion 515 of the drive slot 513, thereby causing the actuation member 502 to rotate and also simultaneously move axially in a distal direction back to the recessed position, thereby causing the guide protrusion 518 to travel along the diagonally extending portion 538 of the guide slot 517 from the circumferentially-extending portion 521 back to the first axially-extending portion. Thus, the device 500 is automatically brought back to the pre-use configuration.

Figure 8A:
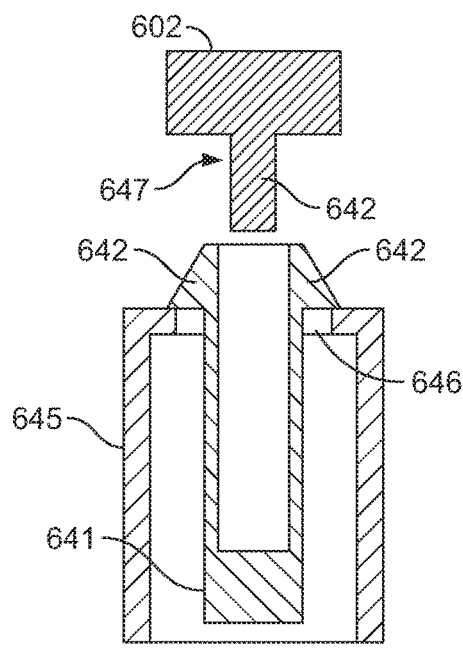
FIG. 8A is a schematic view of parts of a mechanism for automatically moving a needle of a device according to any of the herein disclosed embodiments from the pre-use position to the injecting position.
Figure 8B:
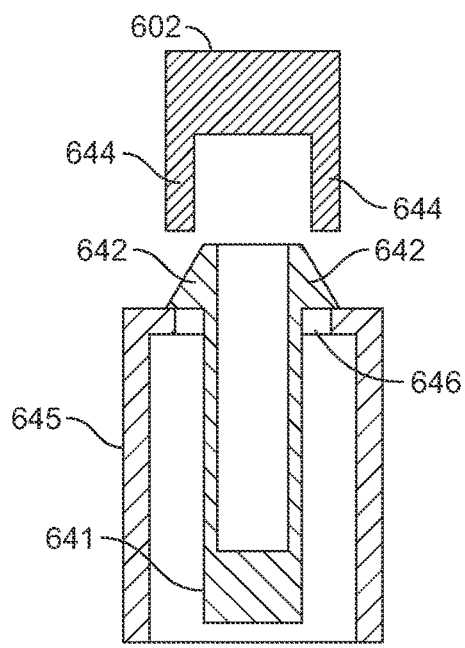
FIG. 8B is a schematic view of FIG. 8A with the actuation member rotated.
Figure 8C:
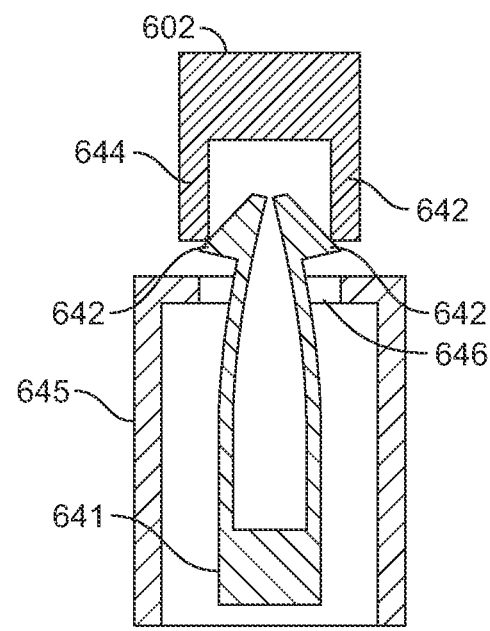
FIG. 8C is a schematic view of FIG. 8A with the actuation member in the actuation position.

FIGS. 8A to 8C show details of part of an example of a mechanism which may be provided in each of the embodiments. Such a mechanism may be actuated or triggered when the actuation member (or actuator) of each embodiment is moved to the actuation position for delivering a dose of medicament, for example for automatically moving a needle of the device from a pre-use position to an injecting position.

The mechanism has a spring and a plunger 641 which is biased distally by the spring. When the actuation member 602 is in the actuation position, the spring is released to move the plunger 641 distally from a proximal position to a distal position, thereby causing a needle of the device to move from a pre-use position in which the needle is recessed within a body of the device to a injecting position for delivering a dose of medicament.

The plunger 641 comprises proximally-extending flexible clips 642.

The actuation member 602 comprises a firing boss 647 for engaging the flexible clips 642 to activate the mechanism for automatically moving the needle from the pre-use position to the injecting position. The firing boss 647 comprises protrusions 642 for engaging the proximally-extending flexible clips 642.

The actuation member 602 is rotatable from a first position in which the protrusions 644 are not axially aligned with the proximally-extending flexible clips 642 as shown, for example, in FIG. 8A, to a second position in which the protrusions 644 are axially aligned with the proximally-extending flexible clips 642 as shown, for example, in FIG. 8B. The actuation member 602 may be rotated relative to the body, as discussed in relation the embodiment discussed above.

When the actuation member 602 is in the first position, it is not possible to activate the mechanism by moving the actuation member 602 distally since the protrusions 644 are not axially aligned with the proximally-extending flexible clips 642. The protrusions 644 cannot engage the proximally-extending flexible clips 642 if the actuation member 602 is moved distally from a protruded position to the actuation position.

In contrast, when the actuation member 602 is in the second position, the mechanism can be activated by moving the actuation member 602 distally since the protrusions 644 are axially aligned with the proximally-extending flexible clips 642. The protrusions 644 engage the proximally-extending flexible clips 642 when the actuation member 602 is moved from the protruded position as shown, for example, in FIG. 8B, to the actuation position as shown, for example, in FIG. 8C.

The medicament delivery device comprises an inner body 645 which contains at least part of the mechanism for automatically moving the needle from the pre-use position to the injecting position.

The one or more clips 642 protrude through an opening 646 in the proximal end of the inner body 645. The one or more clips 642 engage with the inner body 645 for maintaining the plunger 641 in the proximal position. Alternatively, the one or more clips 642 may engage with another component of the device.

When the protrusions 644 engage with the proximally-extending flexible clips 642, as shown for example in FIG. 8C, the protrusions 644 flex the proximally-extending clips 642 radially-inwardly. This allows the clips 642 to move distally through the opening 646, thereby releasing the spring.

As discussed above, the device may in some embodiments comprise a syringe for containing medicament. The syringe comprises the needle. The plunger 641 is connected to the syringe. When the spring is released, the plunger 641 moves the syringe distally. The plunger 641 also move distally within the syringe for dispensing medicament via the needle. Alternatively, the plunger may perform one of the actions of moving the syringe distally or moving distally within the syringe for dispensing medicament via the needle.

LIST OF FEATURES

10—Device
11—Housing
12—Cap
13—Needle sleeve
17—Needle
20—Distal region
21—Proximal region
22—Button
23—Piston
100—Device
101—Actuator
102—Actuation member
103—Temperature-dependent actuator
104—Button
107—Bimetallic strip
119—Body
126—Engagement feature
127—Stop
128—Leg
129—Visual indicator
130—Indication member
131—Window
200—Device
201—Actuator
202—Actuation member
203—Temperature-dependent actuator
205—Needle sleeve
207—Bimetallic strip
219—Body
226—Engagement feature
227—Stop
228—Leg
229—Visual indicator
230—Indication member
231—Window
300—Device
301—Actuator
302—Actuation member
303—Temperature-dependent actuator
304—Button
306—Locking member
307—Bimetallic strip
319—Body
326—Engagement feature
327—Stop
328—Leg
334—Shaft
400—Device
401—Actuator
402—Actuation member
403—Temperature-dependent actuator
404—Button
408—Piston
409—Cylinder
413—Drive slot
414—Protrusion
415—Circumferentially-extending portion of drive slot
416—Axially-extending portion of drive slot
419—Body
435—Abutment surface
500—Device
501—Actuator
502—Actuation member
503—Temperature-dependent actuator
504—Button
508—Piston
509—Cylinder
513—Drive slot
514—Protrusion
515—Circumferentially-extending portion of drive slot
517—Guide slot
518—Guide protrusion
519—Body
520—First axially-extending portion of guide slot
521—Circumferentially-extending portion of guide slot
522—First end of circumferentially-extending portion of guide slot
535—Abutment surface
536—Second axially-extending portion of guide slot
537—Second end of circumferentially-extending portion of guide slot
538—Diagonally-extending portion of guide slot
539—First axially-extending portion of drive slot
540—Second axially-extending portion of drive slot
602—Actuation member
641—Plunger
642—Flexible clips
644—Protrusion
645—Inner body
646—Opening
647—Firing boss
700—Device
775—Distal end
777—Cap
779—Actuation member
781—Body
783—Locking member
785—Syringe
787—Needle
789—Plunger
791—Injection site
795—Stop
797—Bias
799—Bias The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. In some embodiments, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®): B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and method disclosed herein include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
   an actuator comprising a needle sleeve configured to be movable by a user to an actuation position to cause a dose of medicament to be dispensed from the medicament delivery device, the actuator being configured to be movable from (i) a deactivated position in which the user is prevented from moving the needle sleeve to the actuation position to (ii) an activated position in which the needle sleeve is released for movement by the user to the actuation position; and
   a temperature-dependent actuator configured to move the actuator from the deactivated position to the activated position in response to a change in temperature of the temperature-dependent actuator.

2. The medicament delivery device of claim 1, wherein the temperature-dependent actuator comprises a bimetallic strip to cause the actuator to rotate from the deactivated position to the activated position in response to the change in temperature of the temperature-dependent actuator.

3. The medicament delivery device of claim 1, wherein the temperature-dependent actuator comprises a phase change actuator comprising a phase change material configured to change phase in response to the change in temperature of the temperature-dependent actuator.

4. The medicament delivery device of claim 1, wherein the medicament delivery device comprises a container for containing medicament.

5. The medicament delivery device of claim 4, wherein the container is a syringe comprising a needle and containing the dose of medicament.

6. A medicament delivery device comprising:
a body configured to hold a medicament container;
a member configured to rotate relative to the body from (i) a first rotational position in which axial movement of the member relative to the body is limited to (ii) a second rotational position in which axial movement of the member is allowed; and
a temperature-dependent actuator configured to rotate the member from the first rotational position to the second rotational position,
wherein the medicament delivery device is configured such that when the member is in the second rotational position, the member is axially movable relative to the body along a longitudinal axis of the body to cause a medicament to be dispensed from the medicament container.

7. The medicament delivery device of claim 6, wherein the member comprises a button configured to move between (i) a distal position in which a proximal end of the member extends proximally beyond a proximal end of the body by a first distance and (ii) a proximal position in which the proximal end of the member extends proximally beyond the proximal end of the body by a second distance that is greater than the first distance.

8. The medicament delivery device of claim 7, wherein the medicament delivery device is configured such that when the member is in the second rotational position, the member is movable from the proximal position to the distal position to cause the medicament to be dispensed from the medicament container.

9. The medicament delivery device of claim 6, wherein the member comprises a needle sleeve configured to move between (i) a distal position in which a distal end of the member is distal to a distal end of a needle attached to the medicament container and (ii) a proximal position in which the distal end of the needle is distal to the distal end of the member.

10. The medicament delivery device of claim 9, wherein the medicament delivery device is configured such that when the member is in the second rotational position, the member is movable from the distal position to the proximal position to cause the medicament to be dispensed from the medicament container.

11. The medicament delivery device of claim 6, wherein the member is configured to rotate from the first rotational position to the second rotational position without user assistance.

12. A medicament delivery device comprising:
an actuator comprising an actuation member configured to be movable to an actuation position to cause a dose of medicament to be dispensed from the medicament delivery device, the actuator being configured to be movable from (i) a deactivated position in which a movement of the actuation member to the actuation position is limited to (ii) a raised position in which the actuation member is rotatable to a depressible position for allowing the movement of the actuation member to the actuation position; and
a temperature-dependent actuator configured to move the actuator from the deactivated position to the raised position in response to a change in temperature of the temperature-dependent actuator.

13. The medicament delivery device of claim 12, wherein the actuation member comprises a button configured to be depressible by a user to the actuation position.

14. The medicament delivery device of claim 12, wherein the temperature-dependent actuator comprises a piston slidably received within a cylinder.

15. The medicament delivery device of claim 12, wherein the temperature-dependent actuator comprises a phase change actuator comprising a phase change material configured to change phase in response to the change in temperature of the temperature-dependent actuator.

16. The medicament delivery device of claim 12, wherein the medicament delivery device comprises a container for containing medicament.

17. The medicament delivery device of claim 16, wherein the container is a syringe comprising a needle and containing the dose of medicament.

18. A medicament delivery device comprising:
an actuator comprising an actuation member configured to be movable by a user to an actuation position to cause a dose of medicament to be dispensed from the medicament delivery device, the actuator being configured to be movable from (i) a deactivated position in which the user is prevented from moving the actuation member to the actuation position to (ii) a raised position in which the actuation member is rotatable to a depressible position for allowing movement by the user to the actuation position; and
a temperature-dependent actuator configured to move the actuator from the deactivated position to the raised position in response to a change in temperature of the temperature-dependent actuator.

19. The medicament delivery device of claim 18, wherein the actuation member comprises a button configured to be depressible by the user to the actuation position.

20. The medicament delivery device of claim 18, wherein the temperature-dependent actuator comprises a piston slidably received within a cylinder.

21. The medicament delivery device of claim 18, wherein the temperature-dependent actuator comprises a phase change actuator comprising a phase change material configured to change phase in response to the change in temperature of the temperature-dependent actuator.

22. The medicament delivery device of claim 21, wherein the actuation member comprises a drive slot and the temperature-dependent actuator comprises a protrusion slidably received within the drive slot for constraining movement of the protrusion with respect to the drive slot.

23. The medicament delivery device of claim 22, wherein the drive slot comprises a circumferentially-extending portion and a first axially-extending portion such that, when the actuator is in the deactivated position, the protrusion is received within the circumferentially-extending portion of the drive slot such that the temperature-dependent actuator causes the actuation member to move to the raised position in response to the temperature change of the temperature-dependent actuator.

24. The medicament delivery device of claim 23, wherein the medicament delivery device is configured such that moving the actuation member to the raised position allows the actuation member to rotate to the depressible position to thereby cause the protrusion to enter the first axially-extending portion of the drive slot, thereby allowing the actuation member to be depressed by the user from the depressible position to the actuation position.

25. The medicament delivery device of claim 24, wherein the circumferentially-extending portion of the drive slot has an axially-extending component of direction for translating axial movement of the protrusion into rotation of the actuation member to cause the actuation member to rotate to the depressible position.

26. The medicament delivery device of claim 25, wherein:
the actuation member comprises a guide slot comprising an axially-extending portion, and
the medicament delivery device comprises a guide protrusion fixed relative to a body of the medicament delivery device, the guide protrusion located in the guide slot for limiting movement of the actuation member relative to the body.

27. The medicament delivery device of claim 26, wherein the medicament delivery device is configured such that when the protrusion is received within the circumferentially-extending portion of the drive slot, the guide protrusion is located in the axially-extending portion of the guide slot for allowing the actuation member to move axially relative to the body as the temperature-dependent actuator moves the actuator from the deactivated position to the raised position.

28. The medicament delivery device of claim 26, wherein the guide slot comprises a circumferentially-extending portion for permitting rotation of the actuation member, the circumferentially-extending portion of the guide slot having a first end connected to the axially-extending portion of the guide slot.

29. The medicament delivery device of claim 28, wherein the medicament delivery device is configured such that when the temperature-dependent actuator moves the actuator from the deactivated position to the raised position, the guide protrusion is caused to travel from the axially-extending portion of the guide slot along the circumferentially-extending portion of the guide slot so as to cause the actuation member to rotate as the actuation member moves to the raised position.

30. The medicament delivery device of claim 18, wherein the medicament delivery device comprises a container containing the dose of medicament.

* * * * *